US010751224B2

United States Patent
Tsuchiya et al.

(10) Patent No.: US 10,751,224 B2
(45) Date of Patent: Aug. 25, 2020

(54) ANKLE JOINT BANDAGE

(71) Applicant: KOWA COMPANY, LTD., Nagoya-shi (JP)

(72) Inventors: Akiharu Tsuchiya, Chuo-ku (JP); Hitoshi Ojima, Osaka (JP); Hidenori Kaseno, Kahoku (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 879 days.

(21) Appl. No.: 15/123,601

(22) PCT Filed: Mar. 3, 2015

(86) PCT No.: PCT/JP2015/056221
§ 371 (c)(1),
(2) Date: Sep. 2, 2016

(87) PCT Pub. No.: WO2015/133478
PCT Pub. Date: Sep. 11, 2015

(65) Prior Publication Data
US 2017/0079847 A1  Mar. 23, 2017

(30) Foreign Application Priority Data

Mar. 3, 2014  (JP) ................................ 2014-040937
Mar. 6, 2014  (JP) ................................ 2014-043639

(51) Int. Cl.
*A61F 13/00* (2006.01)
*A61F 13/06* (2006.01)
*A61F 5/01* (2006.01)

(52) U.S. Cl.
CPC .......... *A61F 13/066* (2013.01); *A61F 5/0111* (2013.01); *A61F 13/065* (2013.01);
(Continued)

(58) Field of Classification Search
CPC .... A61F 13/066; A61F 13/065; A61F 13/064; A61F 13/067; A61F 15/0111;
(Continued)

(56) References Cited

U.S. PATENT DOCUMENTS 1,443,844 A * 1/1923 Jensen ................... A61F 13/066
602/66
3,699,959 A * 10/1972 Garrahan ............... A61F 13/066
128/DIG. 15
(Continued)

FOREIGN PATENT DOCUMENTS

JP     59-19175 U    2/1984
JP     61-373 A      1/1986
(Continued)

OTHER PUBLICATIONS

International Search Report dated Apr. 21, 2015 in PCT/JP15/056221 Filed Mar. 3, 2015.
(Continued)

*Primary Examiner* — Kim M Lewis
(74) *Attorney, Agent, or Firm* — Oblon, McClelland, Maier & Neustadt, L.L.P.

(57) ABSTRACT

An ankle joint bandage includes a main body part of woven fabric in band shape, an anchor part of woven fabric joined to one end of the main body part and having a loop face of a touch fastener, and an engaging part joined to the other end of the main body part and having a hook face of a touch fastener. The main body part has a winding part which winds around an ankle of a wearer, a first supporting part which extends from an instep to the ankle, and a second supporting part which extends from the ankle to the instep of the wearer to cross the first supporting part at an upper portion of the instep of the wearer, the anchor part fastens around part corresponding to a metatarsal bone of the wearer, and the
(Continued)

engaging part detachably sticks to the loop face of the anchor part.

20 Claims, 16 Drawing Sheets

(52) U.S. Cl.
CPC ............... *A61F 2013/00119* (2013.01); *A61F 2013/00153* (2013.01)

(58) Field of Classification Search
CPC ........ A61F 15/0113; A61F 2013/00119; A61F 2013/00153
USPC .................................. 602/27, 65, 66, 75, 76
See application file for complete search history.

(56) References Cited

U.S. PATENT DOCUMENTS

| | | | | | |
|---|---|---|---|---|---|
| 3,777,751 | A | * | 12/1973 | Wise | A61F 13/066 128/DIG. 15 |
| 4,085,746 | A | * | 4/1978 | Castiglia | A61F 13/066 128/DIG. 15 |
| 4,207,885 | A | * | 6/1980 | Hampton | A61F 13/00021 139/419 |
| 4,367,733 | A | * | 1/1983 | Stromgren | A61F 13/066 602/65 |
| 4,369,775 | A | * | 1/1983 | Gamm | A61F 5/3738 602/62 |
| 4,392,487 | A | * | 7/1983 | Selner | A61F 13/066 602/27 |
| 4,495,942 | A | * | 1/1985 | Palumbo | A61F 13/066 602/27 |
| 4,632,105 | A | * | 12/1986 | Barlow | A61F 13/108 602/64 |
| 4,665,909 | A | * | 5/1987 | Trainor | A61F 13/0273 602/75 |
| 4,753,225 | A | * | 6/1988 | Vogel | A61H 23/0236 601/47 |
| 4,926,848 | A | * | 5/1990 | Shimkus | A61F 13/0273 128/DIG. 15 |
| D403,425 | S | * | 12/1998 | Taylor | A61F 13/066 D24/192 |
| 6,811,540 | B1 | * | 11/2004 | Ritchie | A61F 5/0111 128/882 |
| 7,166,760 | B1 | | 1/2007 | Talbot | |
| 2009/0247921 | A1 | * | 10/2009 | Weitzen | A61F 5/0111 602/27 |
| 2013/0310723 | A1 | | 11/2013 | Yueh-Hua Chiang | |

FOREIGN PATENT DOCUMENTS

| | | |
|---|---|---|
| JP | 2-139623 U | 11/1990 |
| JP | 4-40618 U | 4/1992 |
| JP | 6-80419 U | 11/1994 |
| JP | 2006-15172 A | 1/2006 |
| JP | 3157527 U | 2/2010 |
| JP | 2011-45628 A | 3/2011 |
| JP | 2014-9407 A | 1/2014 |

OTHER PUBLICATIONS

Extended European Search Report dated Oct. 18, 2017 in Patent Application No. 15758930.0.

* cited by examiner

FIG. 5
(a)
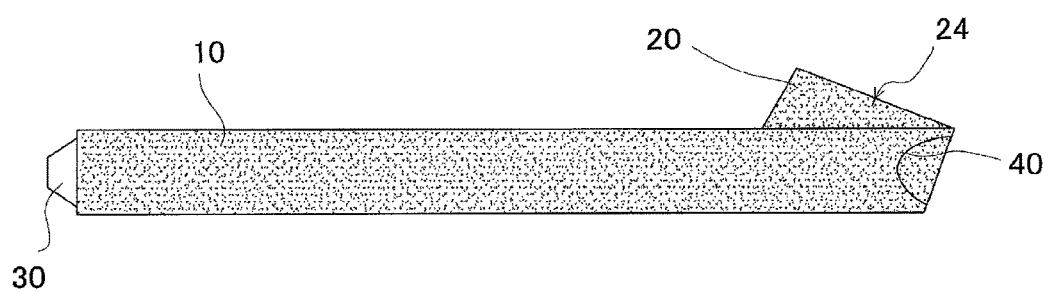
(b)
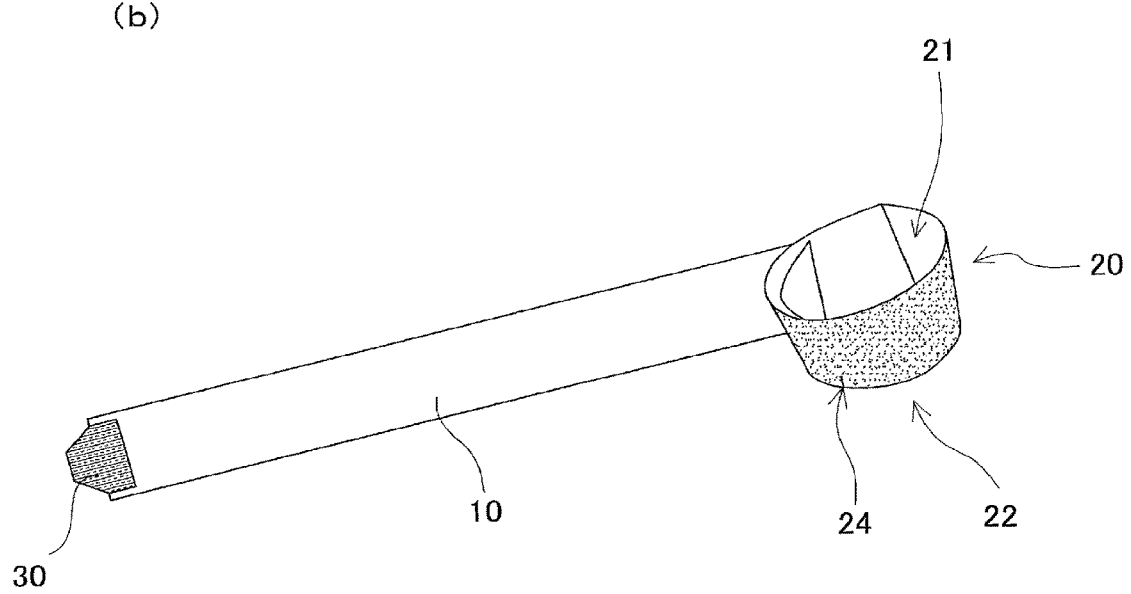

FIG. 6
(a)
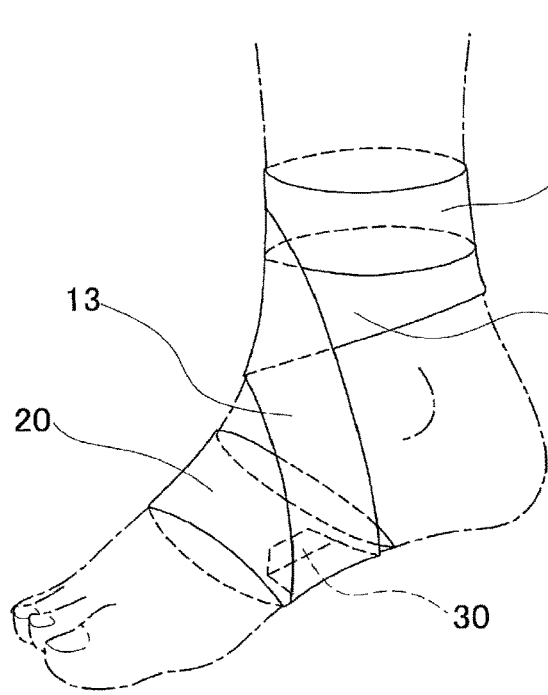
(b)
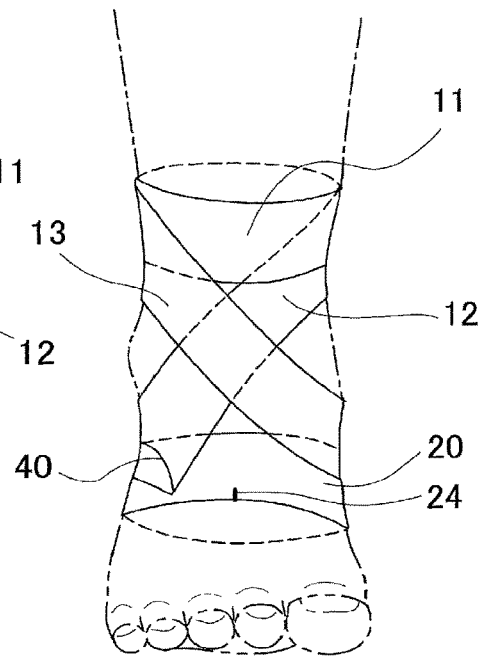
(c)
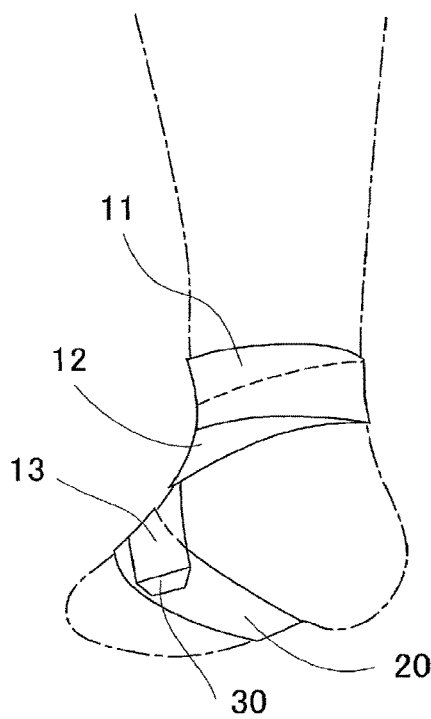
(d)
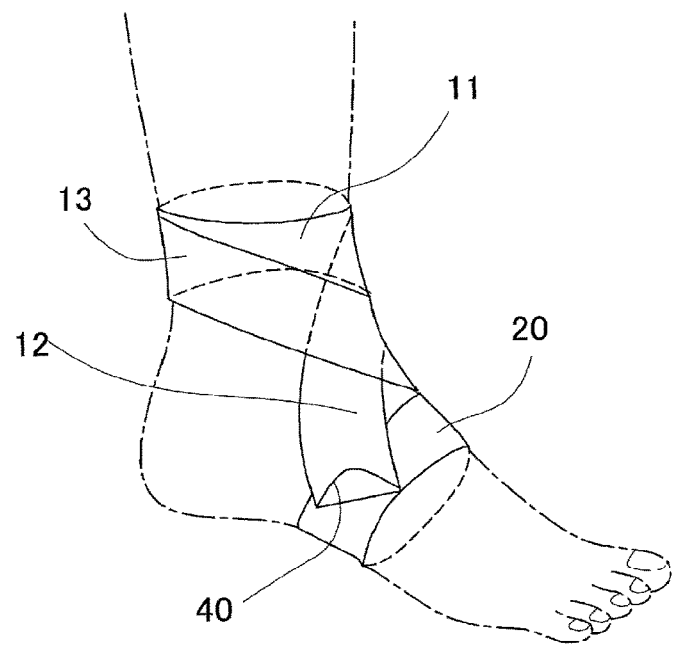

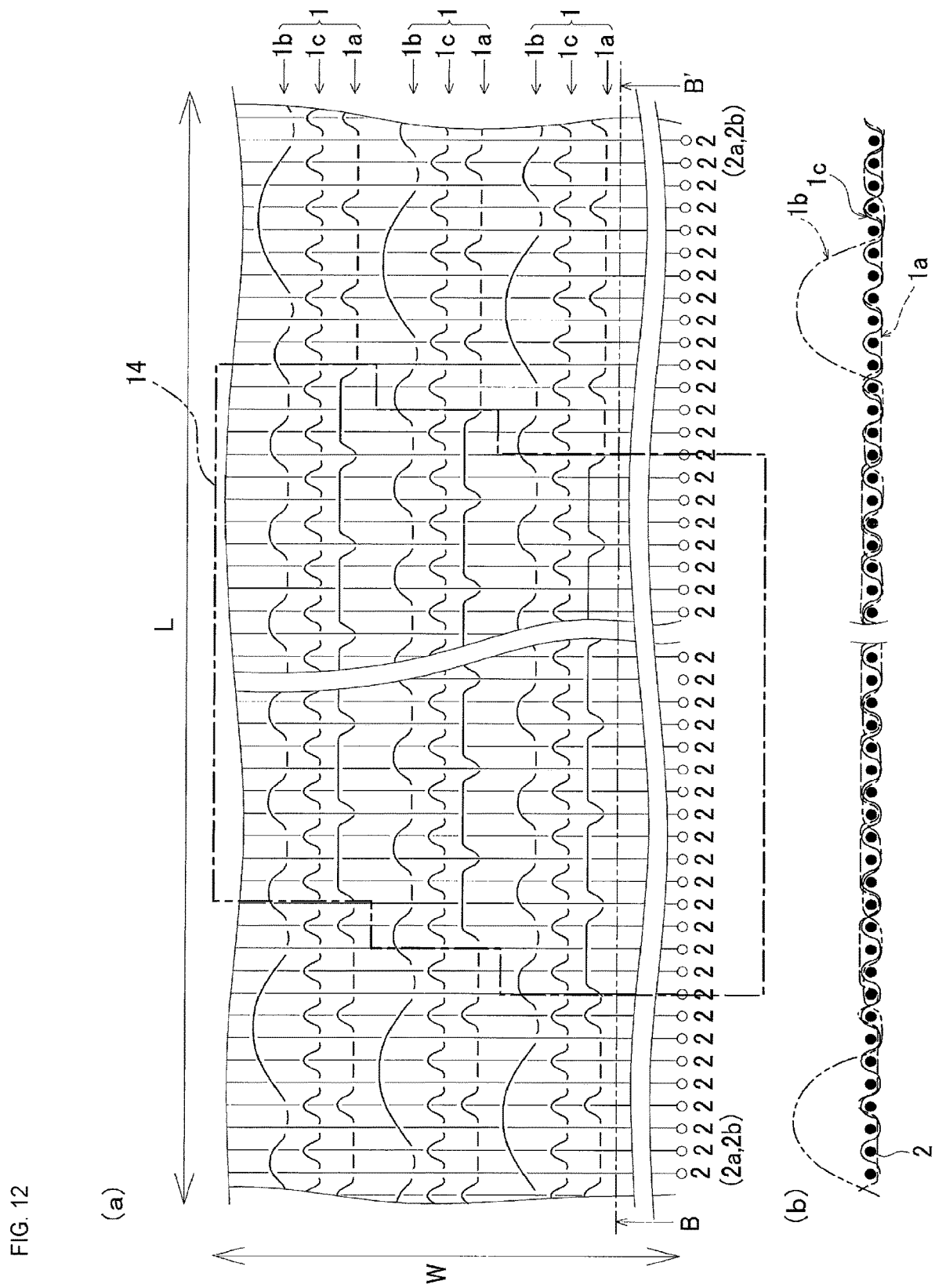

FIG. 13

| Evaluation items | Comparative Example 1 (35%) | Example 1 (45%) | Example 2 (60%) | Example 3 (75%) | Comparative Example 2 (90%) |
|---|---|---|---|---|---|
| ① Fixing force | Considerably strong (2.8 points) | Strong (2.2 points) | Strong (2.0 points) | Weak (1.0 points) | Weak (1.0 points) |
| ② Pain | Painful (1.0 points) | Painful (1.2 points) | Almost painless (1.6 points) | Almost painless (1.6 points) | Painless (2.4 points) |
| ③ Ease of peeling-off of touch fastener | Good (3.0 points) | Good (2.8 points) | Good (2.8 points) | Slightly poor (2.2 points) | Poor (1.2 points) |
| ④ Close contact property of fabric | With floating (1.0 points) | With floating (1.2 points) | Very good (2.8 points) | Very good (3.0 points) | Very good (3.0 points) |
| ⑤ Ease of winding | Hard to wind tightly (1.2 points) | Easy to wind (2.4 points) | Very easy to wind (2.6 points) | Easy to wind (2.4 points) | Extended too much, and thus hard to wind (1.2 points) |
| ⑥ Ease of adjustment of fixing force | Hard to adjust tightly (1.0 points) | Easy to adjust (2.0 points) | Very easy to adjust (2.6 points) | Very easy to adjust (2.6 points) | Very easy to adjust (2.6 points) |
| ⑦ Difficulty of fabric folding | Hard to be folded (3.0 points) | Hard to be folded (3.0 points) | Hard to be folded (2.8 points) | Slightly easy to be folded (2.2 points) | Easy to be folded (1.2 points) |
| Total points | 13.0 points | 14.8 points | 17.2 points | 15.0 points | 12.6 points |
| Average score | 1.86 points | 2.11 points | 2.46 points | 2.14 points | 1.80 points |

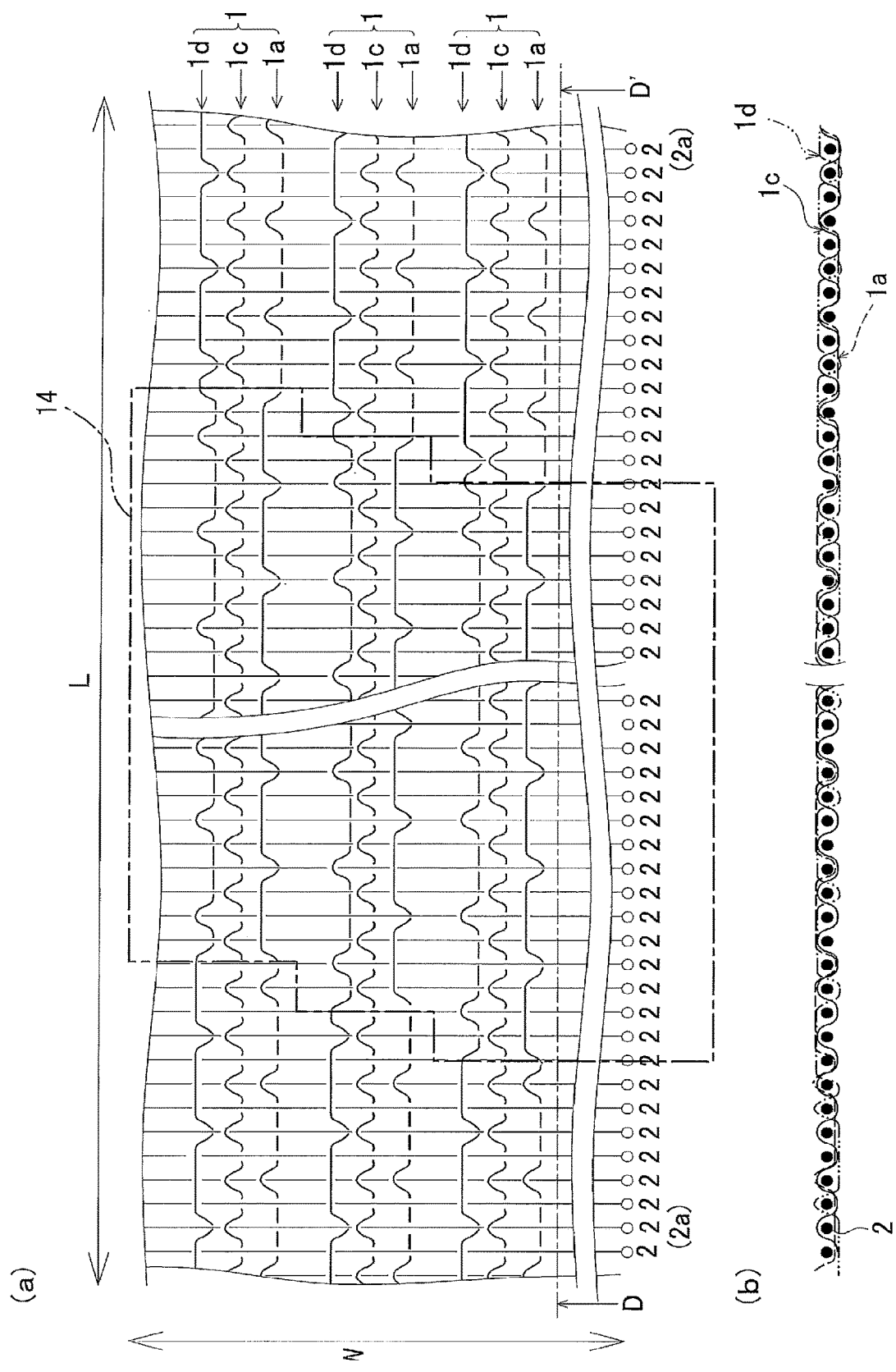

ANKLE JOINT BANDAGE

TECHNICAL FIELD

The present invention relates to an ankle joint bandage which can support the daily motion of a wearer, and in particular, to an ankle joint bandage having a taping function of improving the stability of the ankle joint, thereby reducing fatigue of the triceps surae muscle (the calf) and relieving pain of the Achilles' tendon, the triceps surae muscle, and the outside (the ligament) of the ankle joint.

BACKGROUND ART

In the related art, a band-shaped taping tape (a stretchable or non-stretchable adhesive cloth tape which is used by being stuck to a part of the body), a bandage, a substantially tubular supporter knitted in circular knitting, or the like has been used in order to cope with a medical purpose such as for prevention of an external injury such as a sprain of a wrist joint, an ankle joint, or a knee joint, emergency treatment at the time of the external injury, assistance in rehabilitation after the injury and until complete recovery, or prevention of the recurrence of the external injury or the like.

Of these, the taping tape is disposable, and thereby is not economical, and has a problem in which depending on the constitution of a user, a rash occurs on the skin of the user due to an adhesive, and there is a concern that in a user having sensitive skin, such as an aged person, skin peeling may occur when peeling off the taping tape.

Further, the circular knitting supporter has an approximately tubular shape, and therefore, there is a problem in which there is a concern that in a case where an injured site is inserted to be forcedly bent, it may be painful, and a fixing force is inferior, as compared to the taping tape.

In contrast, the bandage is a band-shaped fabric having stretchability in a warp direction, and therefore, it easily follows an affected area, the wearer themselves can wind it while adjusting a fixing force, an excessive force is not applied against the movement of the wearer's body, a stable fixing force can be obtained, and it is economical because it can be used repeatedly.

For example, an ankle correction implement of the related art is provided with a locking part which is locked to a big toe or another toe, a band-shaped annular winding part which is fixed to be annularly wound around the ankle and has flexibility to expand and contract along a direction of the winding, a band-shaped spiral winding part which connects the locking part and the annular winding part, is spirally wound over an area from the big toe or another toe of the foot to the ankle, and has flexibility to expand and contract along a direction of the winding, and a bending spiral winding part which is bent between the annular winding part, the spiral winding part, and the locking part (refer to PTL 1, for example).

CITATION LIST

Patent Literature

[PTL 1] JP-A-2011-45628

SUMMARY OF INVENTION

Technical Problem

The ankle correction implement of the related art is for correcting the external rotation or the internal rotation of the ankle by being spirally wound over an area from the toe to the ankle with the locking part, into which the big toe or another toe is inserted, as an anchor, and does not aim at taping (a figure-eight) for stabilizing the entire joint of the ankle.

Further, in the ankle correction implement of the related art, the big toe or only one toe of other toes is inserted into the locking part, and therefore, the toe with the locking part put thereon becomes higher by an amount corresponding to the thickness of a cloth of the locking part, as compared to other toes, and thus there is a problem in which a sense of discomfort occurs in the sole of the foot when a wearer walks with the ankle correction implement worn thereon.

Further, in the ankle correction implement of the related art, a material in which cloths (a hook-and-loop fastener cloth and a usual cloth) are joined and fixed to the front and back surfaces of a rubber plate is used for the annular winding part, and thus there is a problem in which the thickness of the annular winding part becomes thicker.

Further, in PTL 1, there is no specific disclosure of the maximum elongation of each of the bending spiral winding part, the annular winding part, and the spiral winding part.

The present invention has been made in order to solve the problem as described above and has an object to provide an ankle joint bandage having a taping function of improving the stability of the ankle joint, thereby being able to enhance the walking performance of a wearer.

Solution to Problem

According to the present invention, there is provided an ankle joint bandage including: a band-shaped main body part which is woven in a fabric and composed of a winding part which is wound around an ankle of a wearer, a first supporting part which is disposed from an instep to the ankle of the wearer, and a second supporting part which is disposed from the ankle to the instep of the wearer to cross the first supporting part at an upper portion of the instep of the wearer; an anchor part which is joined to one end of the main body part, is woven in a fabric having a loop face of a touch fastener, and is fastened around a part corresponding to a metatarsal bone of the wearer; and an engaging part which is joined to the other end of the main body part and has a hook face of a touch fastener, which is detachably stuck to the loop face of the anchor part.

In addition, in the present invention, the expression "being disposed" means "being placed to be applied to a predetermined position of a person (a site of a wearer)", and the expression "being provided" means "being provided at a predetermined position of an object (an ankle joint bandage)".

Advantageous Effects of Invention

In the ankle joint bandage according to the present invention, it is possible to improve the stability of the ankle joint, thereby reducing fatigue of the triceps surae muscle and relieving pain of the Achilles' tendon, the triceps surae muscle, and the outside (the ligament) of the ankle joint.

BRIEF DESCRIPTION OF DRAWINGS

FIG. 5(a) is a front view in which a center mark of the anchor part shown in FIG. 1 is located at the center of the front, and FIG. 5(b) is a perspective view of the ankle joint bandage shown in FIG. 1.

FIG. 6(a) is an explanatory diagram of a wearing state of the ankle joint bandage shown in FIGS. 1 and 4 when viewed from the left front, FIG. 6(b) is an explanatory diagram of the wearing state of the ankle joint bandage shown in FIGS. 1 and 4 when viewed from the front side, FIG. 6(c) is an explanatory diagram of the wearing state of the ankle joint bandage shown in FIGS. 1 and 4 when viewed from the left back, and FIG. 6(d) is an explanatory diagram of the wearing state of the ankle joint bandage shown in FIGS. 1 and 4 when viewed from the right front.

FIG. 12(a) is an explanatory diagram for describing an example of a fabric weave of a loop face and a pattern part of each of the main body part and the anchor part shown in FIG. 2, and FIG. 12(b) is a cross-sectional view taken along line B-B' and viewed in the direction of an arrow, of the fabric weave shown in FIG. 12(a).

FIG. 13 is a table showing the evaluation results of an effect feeling due to a difference in the maximum elongation of the main body part shown in FIG. 1.

FIG. 16(a) is an explanatory diagram for describing an example of a fabric weave of a pattern part of a main body part which does not have a loop face of a touch fastener, and FIG. 16(b) is a cross-sectional view taken along line D-D' and viewed in the direction of an arrow, of the fabric weave shown in FIG. 16(a).

DESCRIPTION OF EMBODIMENTS

First Embodiment of the Present Invention

Figure 1:
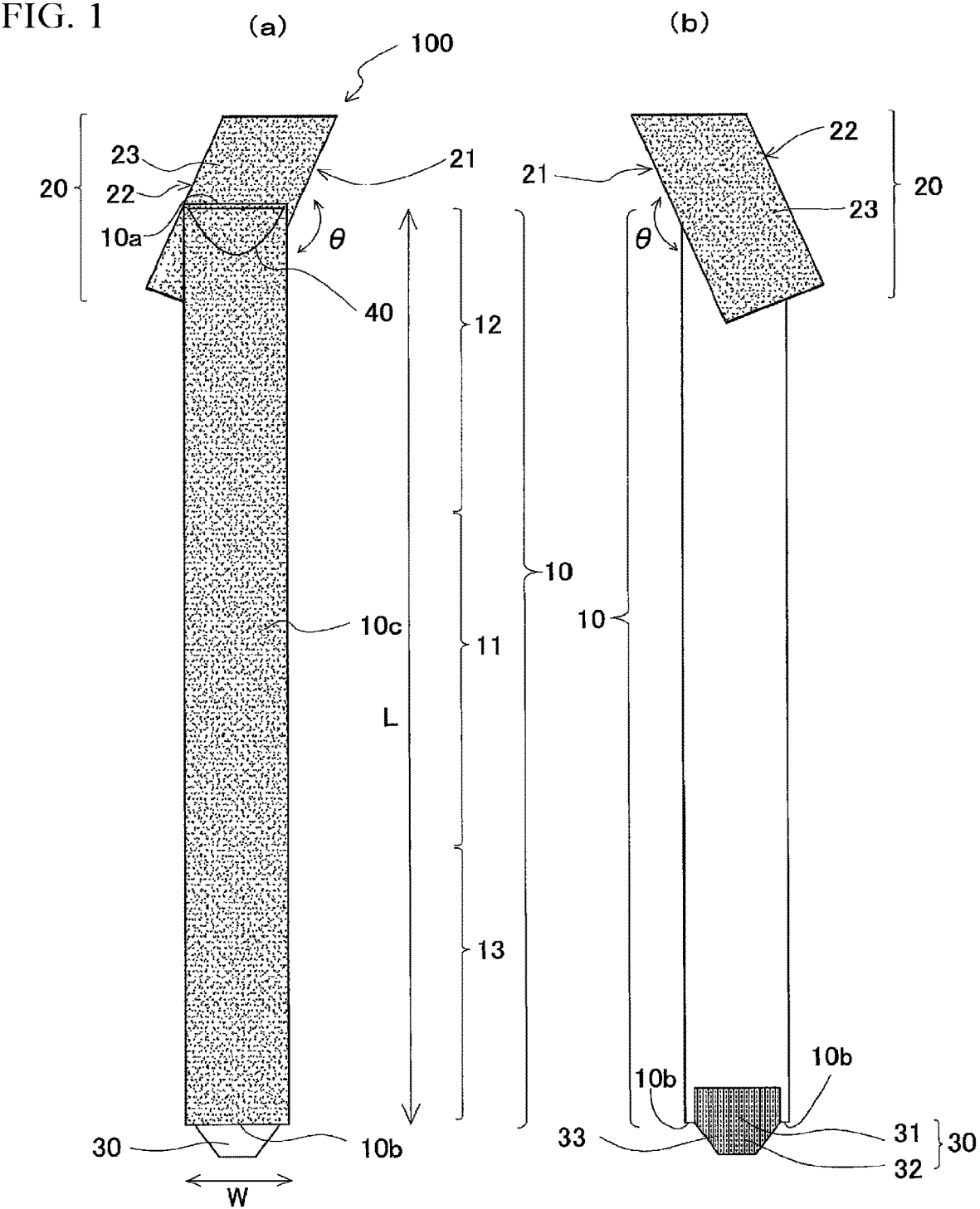
FIG. 1(a) is a front view showing a schematic configuration of an ankle joint bandage for right foot varus sprain prevention according to a first embodiment.
FIG. 1(b) is a back view of the ankle joint bandage shown in FIG. 1(a).

In the present invention, a bandage means a "thing which includes a band-shaped fabric having stretchability in a warp direction as a main material and in which the band-shaped fabric is wound around a part of the body, thereby being able to assist a function of the body", and as long as it has such an effect, even if it is not expressed as a bandage (for example, a taping supporter, a supporter band, or the like), it is within the scope of the bandage according to the present invention.

An ankle joint bandage 100 according to the present invention comprises: a band-shaped main body part 10 which is woven in a fabric having a loop face 10c of a touch fastener and is composed of a winding part 11 which is wound around the ankle of a wearer, a first supporting part 12 which is disposed in a taut state from the instep to the ankle of the wearer, and a second supporting part 13 which is disposed in a taut state from the ankle to the instep of the wearer to cross the first supporting part 12 at an upper portion of the instep of the wearer; an anchor part 20 which is joined to one end 10a of the main body part 10, is woven in a fabric having a loop face 23 of a touch fastener, and is fastened around a part corresponding to the metatarsal bone of the wearer; and an engaging part 30 which is joined to the other end 10b of the main body part 10 and has a hook face 33 of a touch fastener, which is detachably stuck to the loop face 23 of the anchor part 20, as shown in FIGS. 1 to 10.

The anchor part 20 is fastened around a part corresponding to the metatarsal bone of a wearer, thereby positioning the ankle joint bandage 100 with respect to the ankle of the wearer, and serves as a lower anchor of the main body part 10 configuring a figure-eight.

Each of the main body part 10 and the anchor part 20 has a band shape and is made of a narrow stretchable fabric which is woven in combination of a warp 1 and a weft 2 by a power loom such as a needle loom or a jacquard needle loom, has stretchability in a warp direction (a longitudinal direction L or a circumferential direction), and is inhibited in stretchability in a weft direction (a width direction W).

Further, the main body part 10 is composed of the winding part 11 which is wound around the ankle of a wearer, the first supporting part 12 which is disposed in a taut state from the instep to the ankle of the wearer, and the second supporting part 13 which is disposed in a taut state from the ankle to the instep of the wearer to cross the first supporting part 12 at an upper portion of the instep of the wearer, in which the first supporting part 12 is provided on the one end 10a side of the main body part 10, the second supporting part 13 is provided on the other end 10b side of the main body part 10, the winding part 11 is provided between the first supporting part 12 and the second supporting part 13, and the first supporting part 12, the winding part 11, and the second supporting part 13 have straight line shapes having the same width.

Figure 11:
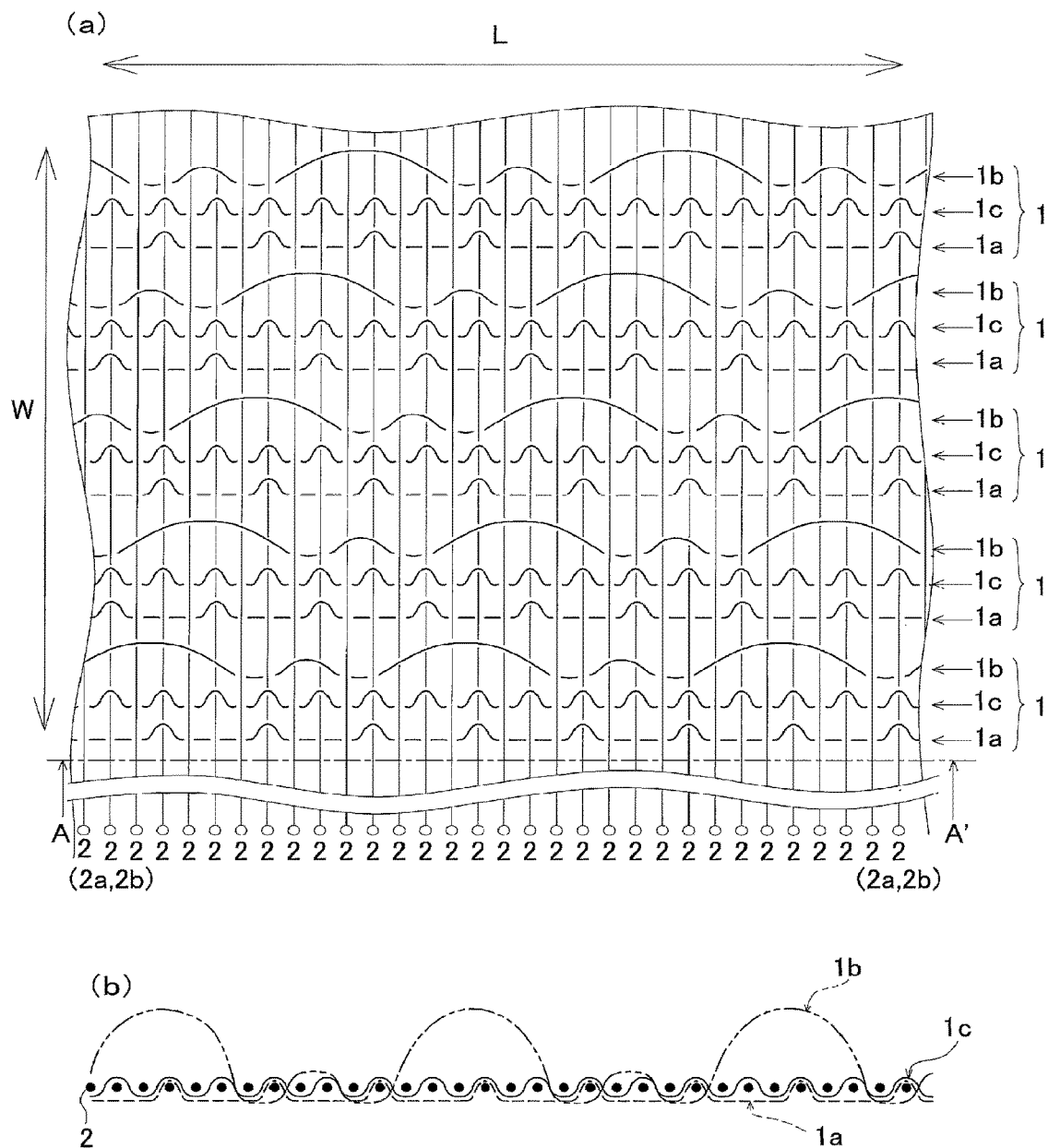
FIG. 11(a) is an explanatory diagram for describing an example of a fabric weave of a loop face of each of the main body part and the anchor part shown in FIG. 1.
FIG. 11(b) is a cross-sectional view taken along line A-A' and viewed in the direction of an arrow, of the fabric weave shown in FIG. 11(a).

Further, the warp 1 of each of the main body part 10 and the anchor part 20 is provided with a warp ground yarn 1a which configures one face (for example, a back ground face) of a fabric along with the weft 2, a pile yarn 1b which forms loops on the other face (for example, a front ground face) of the fabric by floating on a plurality of wefts 2 adjacent to each other in the warp direction, and an elastic yarn 1c which provides stretchability in the warp direction, as shown in FIG. 11. Hereinafter, in this specification, each of a face having the loop face 10c of the main body part 10 and a face having the loop face 23 of the anchor part 20 is referred to as a "front ground face", and a back face thereof is referred to as a "back ground face".

The weft 2 is provided with a weft ground yarn 2a which configures the back ground face of the fabric along with the warp ground yarn 1a, and a fusion yarn 2b which is provided parallel to the weft ground yarn 2a and has thermal adhesiveness, and a single piece of weft ground yarn 2a and a single piece of fusion yarn 2b are provided in parallel, thereby configuring a single piece of weft 2. Further, in FIGS. 11 and 12, a single piece of weft ground yarn 2a and a single piece of fusion yarn 2b are shown as a single piece of weft 2. Further, in FIGS. 11(b) and 12(b), on the basis of the wefts 2 which are provided in parallel, the upper side is the front ground face and the lower side is the back ground face.

Figure 2:
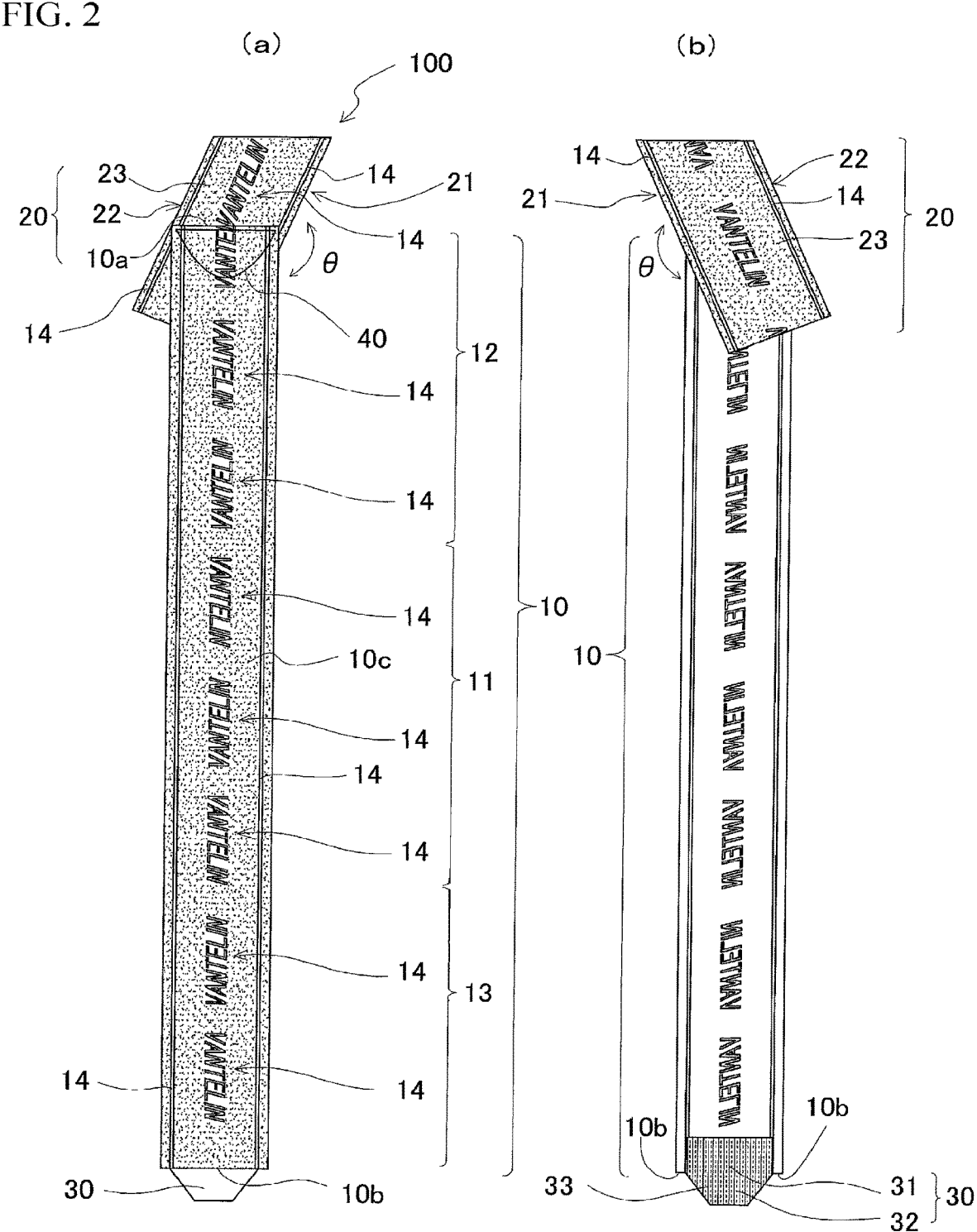
FIG. 2(a) is a front view showing a schematic configuration of an ankle joint bandage in which patterns are formed in a main body part and an anchor part shown in FIG. 1.
FIG. 2(b) is a back view of the ankle joint bandage shown in FIG. 2(a).

Further, in each of the main body part 10 and the anchor part 20, a pattern 14 composed of characters, figures, symbols, or a combination thereof can be partially formed in the front ground face in a jacquard weave which is freely opened, as shown in FIG. 2, by making the warp ground yarn 1a of the warp 1 float to the front ground face side and making the pile yarn 1b of the warp 1 sink to the back ground face, with respect to the plurality of wefts 2 adjacent to each other in the warp direction (the longitudinal direction L), by using a jacquard needle loom, and the main body part 10 and the anchor part 20 have loops (the loop face 10c and the loop face 23) on substantially the entire surface of the front ground face with the exception of the regions of the patterns 14.

Next, an example of a fabric weave of each of the main body part 10 and the anchor part 20 according to this embodiment will be described by using FIG. 11. That is, the warp ground yarn 1a forming the loop face 10c (the loop face 23) configures a fabric weave by repeating 1-3 float-sink with respect to the weft 2 (the weft ground yarn 2a and the fusion yarn 2b), in which the warp ground yarn 1a floats so as to pass on the upper side with respect to a single piece of weft 2 (weft ground yarn 2a and fusion yarn 2b) and sinks so as to pass on the lower side with respect to three pieces of wefts 2 (weft ground yarns 2a and fusion yarns 2b) adjacent to each other, as shown in FIG. 11(b).

Further, the pile yarn 1b forming the loop face 10c (the loop face 23) configures a fabric weave by repeating 6-2-2-2 float-sink with respect to the weft 2 (the weft ground yarn 2a and the fusion yarn 2b), in which the pile yarn 1b floats so as to pass on the upper side with respect to six pieces of wefts 2 (weft ground yarns 2a and fusion yarns 2b) adjacent to each other, sinks so as to pass on the lower side with respect to two pieces of wefts 2 (weft ground yarns 2a and fusion yarns 2b) adjacent to each other, floats so as to pass on the upper side with respect to two pieces of wefts 2 (weft ground yarns 2a and fusion yarns 2b) adjacent to each other, and sinks so as to pass on the lower side with respect to two pieces of wefts 2 (weft ground yarns 2a and fusion yarns 2b) adjacent to each other, as shown in FIG. 11(b).

Further, the elastic yarn 1c forming the loop face 10c (the loop face 23) configures a fabric weave by repeating 1-1 float-sink with respect to the weft 2 (the weft ground yarn 2a and the fusion yarn 2b), in which the elastic yarn 1c floats so as to pass on the upper side with respect to a single piece of weft 2 (weft ground yarn 2a and fusion yarn 2b) and sinks so as to pass on the lower side with respect to a single piece of weft 2 (weft ground yarn 2a and fusion yarn 2b), as shown in FIG. 11(b).

In addition, the fabric weave composed of the warp ground yarn 1a, the pile yarn 1b, and the elastic yarn 1c shown in FIG. 11 is an example, and as long as it is possible to have loops (the loop face 10c or the loop face 23) on the front ground face, there is no limitation to this fabric weave.

Subsequently, an example of a fabric weave of the pattern 14 which is formed in the main body part 10 according to this embodiment will be described by using FIG. 12. That is, the warp ground yarn 1a forming the pattern 14 configures a fabric weave by repeating 3-1 float-sink with respect to the weft 2 (the weft ground yarn 2a and the fusion yarn 2b), in which the warp ground yarn 1a floats so as to pass on the upper side with respect to three pieces of wefts 2 (weft ground yarns 2a and fusion yarns 2b) adjacent to each other and sinks so as to pass on the lower side with respect to a single piece of weft 2 (weft ground yarn 2a and fusion yarn 2b), as shown in FIG. 12(b).

Further, the pile yarn 1b forming the pattern 14 configures a fabric weave by repeating 2-2 float-sink with respect to the weft 2 (the weft ground yarn 2a and the fusion yarn 2b), in which the pile yarn 1b sinks so as to pass on the lower side with respect to two pieces of wefts 2 (weft ground yarns 2a and fusion yarns 2b) adjacent to each other and floats so as to pass on the upper side with respect to two pieces of wefts 2 (weft ground yarns 2a and fusion yarns 2b) adjacent to each other, as shown in FIG. 12(b).

Further, the elastic yarn 1c forming the pattern 14 configures a fabric weave by repeating 1-1 float-sink with respect to the weft 2 (the weft ground yarn 2a and the fusion yarn 2b), in which the elastic yarn 1c floats so as to pass on the upper side with respect to a single piece of weft 2 (weft ground yarn 2a and fusion yarn 2b) and sinks so as to pass on the lower side with respect to a single piece of weft 2 (weft ground yarn 2a and fusion yarn 2b), as shown in FIG. 12(b).

In addition, the fabric weave composed of the warp ground yarn 1a, the pile yarn 1b, and the elastic yarn 1c shown in FIG. 12 is an example, and as long as it is possible to form the pattern 14 in the loop face 10c or 23 of the front ground face, there is no limitation to this fabric weave.

Further, in each of the main body part 10 and the anchor part 20, it is possible to freely adjust the maximum elongation in the warp direction (the longitudinal direction L) by the quality of the materials of the warp 1 and the weft 2 (in particular, the thicknesses of the elastic yarn 1c and the weft ground yarn 2a) and the number of times of picking (the number) of the weft 2. In the present invention, the maximum elongation refers to the "percentage of the difference between the longest length (an elongation dimension) when having been stretched with the highest load and the original length (a lay-flat size) with respect to the original length".

In particular, from the results of the overall determination of a sensory evaluation which will be described later, it is preferable that the maximum elongation in the warp direction (the longitudinal direction L) of each of the main body part 10 and the anchor part 20 is set to be in a range of 40% to 80%, and a range of 45% to 75% is more preferable, and the most preferred is 60%.

Here, embodiments of the main body part 10 and the anchor part 20, in each of which the maximum elongation is set to be 60%, will be described. With respect to the warp ground yarn 1a of each of the main body part 10 and the anchor part 20 according to this embodiment, a woolly nylon two-fold yarn having a thickness of 100 counts is preferable, and in each of the main body part 10 and the anchor part 20 according to this embodiment, it is preferable to use 132 pieces of woolly nylon two-fold yarns.

Further, the pile yarn 1b of each of the main body part 10 and the anchor part 20 according to this embodiment is a special textured yarn (210D-10F) obtained by twisting 10 pieces of nylon filaments together, then applying heat thereto, and further performing twisting in a direction opposite to the twisting direction of the 10 pieces of nylon filaments, and having a thickness of 210 deniers, and in each of the main body part 10 and the anchor part 20 according to this embodiment, it is preferable to use 132 pieces of special textured yarns (210D-10F).

Further, with respect to the elastic yarn 1c of each of the main body part 10 and the anchor part 20 according to this embodiment, a polyurethane yarn having a thickness of 560 deniers is preferable, and in each of the main body part 10 and the anchor part 20 according to this embodiment, it is preferable to use 36 pieces of polyurethane yarns.

That is, in each of the main body part 10 and the anchor part 20 in the quality of the material of the warp 1 described above, for example, if a width is 5 cm, warp density by the warps 1 (the warp ground yarns 1a, the pile yarns 1b, and the elastic yarns 1c) is 1485.6 D/mm(=((210D×132 pieces)+(100D×2 pieces×132 pieces)+(560D×36 pieces))/50 mm).

Further, in the pile yarn 1b of each of the main body part 10 and the anchor part 20 according to this embodiment, a filament count is 10 pieces, whereby there is an advantage that, compared to a case where a filament count is a low count (for example, 7 pieces), an adhesive force between dense filaments is high and a feel of the fabric (each of the main body part 10 and the anchor part 20) is soft.

Further, the elastic yarn 1c of each of the main body part 10 and the anchor part 20 according to this embodiment has a thickness of 560 deniers, thereby making the thickness of the fabric (each of the main body part 10 and the anchor part 20) thin, compared to the case of a thick elastic yarn (for example, 1120 deniers), and thus it is possible to soften the fabric itself.

Further, with respect to the weft ground yarn 2a of each of the main body part 10 and the anchor part 20 according to this embodiment, it is preferable to use a single piece of polyester woolly yarn (EW) having a thickness of 150 deniers.

Further, with respect to the fusion yarn 2b of each of the main body part 10 and the anchor part 20 according to this embodiment, it is preferable to use a single piece of nylon thermal fusion yarn (for example, "Elder (registered trademark)" manufactured by Toray Industries, Inc.) having a thickness of 100 deniers.

Further, in each of the main body part 10 and the anchor part 20 according to this embodiment, a single piece of weft ground yarn 2a and a single piece of fusion yarn 2b are simultaneously picked as the weft 2 by a power loom, and the number of times of picking (the number) of the weft 2 (the weft ground yarn 2a and the fusion yarn 2b) is 36.9 times (each 36.9 pieces) per 2.54 cm (1 inch).

That is, in each of the main body part 10 and the anchor part 20 in the quality of material and the number of times of picking (the number) of the weft 2 described above, weft density by the wefts 2 (the polyester woolly yarns and the nylon thermal fusion yarns) is 9225D/inch (=(150D+100D)×36.9 times/inch).

Further, the weft ground yarn 2a of the weft 2 of each of the main body part 10 and the anchor part 20 according to this embodiment has a thickness of 150 deniers, whereby it is possible to make the thickness of the fabric (each of the main body part 10 and the anchor part 20) thin, compared to the case of a weft ground yarn (for example, 300 deniers) which is a thick weft.

In this manner, in each of the main body part 10 and the anchor part 20 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L or the circumferential direction) to be 60%.

Further, with respect to the thickness of the elastic yarn 1c according to this embodiment, 560 deniers has been given as an example. However, in the present invention, available (mass-producible) 420 deniers which is a thickness lower by 1 rank, or 1120 deniers which is a thickness higher by 1 rank may be selected, and the thickness and the number of times of picking (the number) of the weft 2 described above may be changed. That is, if the thickness of the elastic yarn 1c according to this embodiment is in a range of 420 deniers to 1120 deniers, it is possible to set the maximum elongation in the warp direction of each of the main body part 10 and the anchor part 20 to be the maximum elongation within the above-described range.

Further, with respect to the thickness of the weft ground yarn 2a of the weft 2 according to this embodiment, 150 deniers has been given as an example. However, in the present invention, available (mass-producible) 100 deniers which is a thickness lower by 1 rank, or 300 deniers which is a thickness higher by 1 rank may be selected, and the thickness of the elastic yarn 1c and the number of times of picking (the number) of the weft 2 described above may be changed. That is, if the thickness of the weft ground yarn 2a of the weft 2 according to this embodiment is in a range of 100 deniers to 300 deniers, it is possible to set the maximum elongation in the warp direction of each of the main body part 10 and the anchor part 20 to be the maximum elongation within the above-described range.

Further, with respect to the number of times of picking (the number) of the weft 2 (the weft ground yarn 2a and the fusion yarn 2b) according to this embodiment, 36.9 times (each 36.9 pieces) per 2.54 cm (1 inch) has been given as an example. However, in the present invention, the number of times of picking (the number) of the weft 2 (the weft ground yarn 2a and the fusion yarn 2b) in a range of 32.8 times (each 32.8 pieces) per 2.54 cm to 41.0 times (each 41.0 pieces) per 2.54 cm may be selected, and the thicknesses of the elastic yarn 1c and the weft 2 described above may be changed. That is, if the number of times of picking (the number) of the weft 2 (the weft ground yarn 2a and the fusion yarn 2b) according to this embodiment is in a range of 32.8 times (each 32.8 pieces) per 2.54 cm to 41.0 times (each 41.0 pieces) per 2.54 cm, it is possible to set the maximum elongation in the warp direction of each of the main body part 10 and the anchor part 20 to be the maximum elongation within the above-described range.

Further, in a case where the thickness of the main body part 10 is too thick, when winding the bandage around the ankle of a wearer, it becomes bulky, and thus it becomes difficult to wind it, and in a case where the thickness of the main body part 10 is too thin, the fabric itself of the bandage is easily foldable, and thus a desired fixing force is not obtained. For this reason, it is preferable that the thickness of the main body part 10 is set to be a thickness in which it is easy to wind the bandage and a desired fixing force is obtained, and for example, if the maximum elongation in the warp direction (the longitudinal direction L) of the main body part 10 is 60%, it is preferable to set the thickness of the main body part 10 to be less than or equal to 3 mm.

Further, in a case where the thickness of the anchor part 20 is too thick, a sense of discomfort occurs in the sole of the foot of a wearer, and in a case where the thickness of the anchor part 20 is too thin, the fabric itself of the bandage is easily foldable, and thus a desired fixing force is not obtained. For this reason, it is preferable that the thickness of the anchor part 20 is set to be a thickness in which a sense of discomfort does not occur in the sole of the foot of a wearer and a desired fixing force is obtained, and if the maximum elongation in the warp direction (the longitudinal direction L) of the anchor part 20 is 60%, it is preferable to set the thickness of the anchor part 20 to be less than or equal to 3 mm.

Further, in the anchor part 20 according to this embodiment, the loops (the loop face 23) are provided on a face (the front ground face) which becomes the outside in a case where the anchor part 20 is fastened around a part corresponding to the metatarsal bone of a wearer, and therefore, the engaging part 30 (the hook face 33) provided at the main body part 10 is provided on the back ground face side of the other end 10b of the main body part 10 in terms of the ease of attachment and detachment and the degree of freedom of an engaging position.

Further, in the main body part 10, in order to configure a figure-eight and an upper anchor part, the lengths of portions (the first supporting part 12 and the second supporting part 13) which cross each other at the instep of a wearer, and the length of a portion (the winding part 11) which circles around the ankle of the wearer at least once are required, and although there is an individual difference in the size of the ankle according to gender, age, or the like, it is conceivable that the length of the main body part 10 is set to in a range of 46 cm to 48 cm, for example. Further, in the main body part 10, a certain level of width is required in order to effectively perform the fixing of the ankle joint of the wearer, and it is preferable to set the width to be in a range of 3 cm to 7 cm, for example. Further, in the anchor part 20, a certain level of width is required in order to increase the contact area with a foot region of a wearer, thereby increasing a frictional force, and prevent position shift of the anchor part 20 with respect to the foot region of the wearer, and it is preferable to set the width to be in a range of 3 cm to 7 cm, for example.

Further, the main body part 10 according to this embodiment is woven in a fabric having the loop face 10c of a touch fastener by using the same cloth as the anchor part 20. However, if the maximum elongation in the warp direction (the longitudinal direction L) is a desired maximum elongation, the loop face 10c of a touch fastener is not necessarily required.

However, the main body part 10 is woven in a fabric having the loop face 10c of a touch fastener, whereby compared to a case where it does not have the loop face 10c, when being in non-use, it is possible to compactly store the ankle joint bandage 100 by rolling it and making the hook face 33 of the engaging part 30 be engaged with the loop face 10c of the main body part 10, and depending on a wearer, there is also a case of using the ankle joint bandage 100 with the hook face 33 of the engaging part 30 be engaged with the main body part 10, and thus a degree of freedom can be provided in a use method (an engaging position) of the ankle joint bandage 100.

Further, the anchor part 20 according to this embodiment is formed in a ring shape by joining (for example, sewing) both ends of a band-shaped body which is a stretchable fabric, to each other, and in particular, the band-shaped body before the joining of both ends has an isosceles trapezoidal shape, and both ends (sides of the trapezoidal shape) are joined to each other, whereby the band-shaped body after the joining of both ends has the form of a substantially conical tube.

In this way, in the ankle joint bandage 100, in a case where the tiptoe of a wearer has been inserted into the anchor part 20, the inner surface of the anchor part 20 is fitted to the slope of the instep, whereby it is possible to suppress the occurrence of floating or wrinkles in a large-diameter portion 21 and a small-diameter portion 22 of the substantially conical tube of the anchor part 20.

Further, in the anchor part 20, in order to insert the tiptoe of a wearer therein and fasten it around a part corresponding to the metatarsal bone, it is preferable that, for example, the length of a lower base of the trapezoid in the band-shaped body before the joining of both ends (the circumferential length of the large-diameter portion 21 of the substantially conical tube after the joining of both ends) is set to be in a range of 17 cm to 21 cm, and the length of an upper base of the trapezoid in the band-shaped body before the joining of both ends (the circumferential length of the small-diameter portion 22 of the substantially conical tube after the joining of both ends) is set to be in a range of 14 cm to 18 cm.

Here, in the anchor part 20, in a case where a difference in circumferential length between the large-diameter portion 21 and the small-diameter portion 22 of the substantially conical tube after the joining of both ends is greater than or equal to 4 cm, even if the large-diameter portion 21 is fitted to the foot of a wearer, since the circumferential length of the small-diameter portion 22 is small, the small-diameter portion 22 compresses the foot of the wearer, and conversely, even if the small-diameter portion 22 is fitted to the foot of the wearer, since the circumferential length of the large-diameter portion 21 is large, a gap occurs between the foot of the wearer and the large-diameter portion 21.

For this reason, in the anchor part 20, it is preferable that a difference in circumferential length between the large-diameter portion 21 and the small-diameter portion 22 of the substantially conical tube after the joining of both ends is set to be less than 4 cm, preferably, be in a range of 2.5 cm to 3.5 cm, and in particular, in the anchor part 20 according to this embodiment, a difference in circumferential length between the large-diameter portion 21 and the small-diameter portion 22 of the substantially conical tube after the joining of both ends is set to be 3 cm.

Further, as the types of sewing, there are flat seamer sewing (four-needle sewing), overlock sewing, three-point zigzag sewing, and the like. However, both ends of the anchor part 20 according to this embodiment are sewn to each other with the flat seamer sewing which has the advantage that a combined portion becomes thinner, a seam is finished to be flat and strong with a force pressing the seam, and it is easy to conform to a three-dimensional shape by cutting in a mountain shape, and because there is no seam allowance on the back face of a cloth, a sewing point does not touch the skin, and thus a feeling of wearing is good.

Further, the anchor part 20 is formed in the form of a ring in which a circumferential length cannot be adjusted, by sewing both ends of a band-shaped body to each other. However, the anchor part 20 may be made such that the circumferential length thereof can be adjusted, by sewing a hook face of a touch fastener to the back ground face of one end of the band-shaped body without sewing both ends of the band-shaped body to each other.

However, sewing the hook face of a touch fastener to the anchor part 20 causes an increase in manufacturing cost of the ankle joint bandage 100 due to an increase in the number of members, and the thickness of the anchor part 20 in a touch fastener part becomes thicker, thereby impairing a feeling of wearing and a sense of beauty of the ankle joint bandage 100. Therefore, it is preferable to sew both ends of the band-shaped body to each other.

Further, the anchor part 20 and the main body part 10 according to this embodiment are joined to each other with an angle θ between the circumferential direction of the anchor part 20 and the longitudinal direction L of the main body part 10 being 155°, as shown in FIG. 1. However, if the main body part 10 can configure a figure-eight in a case where the ankle joint bandage 100 has been worn, there is no limitation to the above angle θ.

Further, in a case of pulling the main body part 10 from one end 10a to the other end 10b side, the closer the angle θ is to 180°, the more a force acts in the circumferential direction (the longitudinal direction) of the anchor part 20, whereby the anchor part 20 rotates, and the closer the angle θ is to 90°, the more a force acts in the width direction of the anchor part 20, whereby the anchor part 20 rides up along the instep. For this reason, it is preferable that the range of the angle θ is set to be in a range of 145° to 165° in consideration of the ease of a use method of the ankle joint bandage 100 such that in a case of pulling the main body part 10 from one end 10a to the other end 10b side, the main body part 10 can be pulled diagonally backward with respect to the anchor part 20 in a state where floating does not occur in the anchor part 20 and the main body part 10 is not twisted in the vicinity of a joining portion 40.

Further, the joining portion 40 between the anchor part 20 and one end 10a of the main body part 10 is sewn convexly to the other end 10b side of the main body part 10 so as to become longer than the length in the width direction W of the main body part 10.

In this manner, in the ankle joint bandage 100, the joining portion 40 is sewn in a shape convex toward the other end 10b side of the main body part 10, whereby in a case of winding the ankle joint bandage 100 around the ankle joint of a wearer, a twist at the joining portion 40 can be absorbed in response to the winding (pulling) direction of the main body part 10 and the occurrence of floating or wrinkles in the vicinity of the joining portion 40 can be suppressed.

Further, in a case where the joining portion 40 is formed in a substantially triangular shape, when a wearer wears the ankle joint bandage 100, stress is concentrated on the vertex of the triangle due to the tensile stress from the main body part 10, and the cloth of the vertex portion is weakened, and thus there is a concern that the sewn place may collapse.

For this reason, the joining portion 40 according to this embodiment is formed in a substantially semicircular shape, whereby stress does not concentrate even with respect to the tensile stress from the main body part 10, the collapse of the sewn place can be prevented, it is also possible to cope with an individual differences in the pulling direction of the main body part 10, and it is possible to suppress the occurrence of floating or wrinkles in the vicinity of the joining portion 40.

Further, in the joining between the anchor part 20 and one end 10a of the main body part 10, sewing is not performed on both sides of the main body part 10, whereby both sides of the main body part 10 are not fixed to the anchor part 20 and the fabrics in both sides in the vicinity of the joining portion 40 of the main body part 10 can be extended.

For this reason, in the ankle joint bandage 100 according to this embodiment, even if a winding angle of the main body part 10 with respect to the ankle of a wearer changes somewhat, distortion of the fabric in each side in the vicinity of the joining portion 40 of the main body part 10 is absorbed, and thus it is possible to suppress the occurrence of floating or wrinkles of the cloth in each side in the vicinity of the joining portion 40 of the main body part 10.

Further, in the ankle joint bandage 100 according to this embodiment, as shown in FIG. 5(a), a center mark 24 by a seam as a mark can be sewn in the vicinity of the joining portion 40 of the anchor part 20 such that the anchor part 20 is fastened at a correct position of the foot of a wearer and a correct winding method on the ankle joint of the wearer, in which the main body part 10 configures a figure-eight, is obtained.

The engaging part 30 according to this embodiment has a planar shape of a combination of, for example, a rectangle and an isosceles trapezoid, as shown in FIG. 1(b), in which a rectangular portion 31 is sewn to the back ground face of the main body part 10 and an isosceles trapezoid portion 32 protrudes from the other end 10b of the main body part 10. In this manner, in the engaging part 30, the isosceles trapezoid portion 32 protrudes from the other end 10b of the main body part 10, thereby becoming thinner by an amount that does not overlap the main body part 10, whereby it is easy to grip the isosceles trapezoid portion 32 with the fingers of a wearer, and thus it is possible to easily attach and detach the hook face 33 with respect to the loop face 23 of the anchor part 20.

Figure 7:
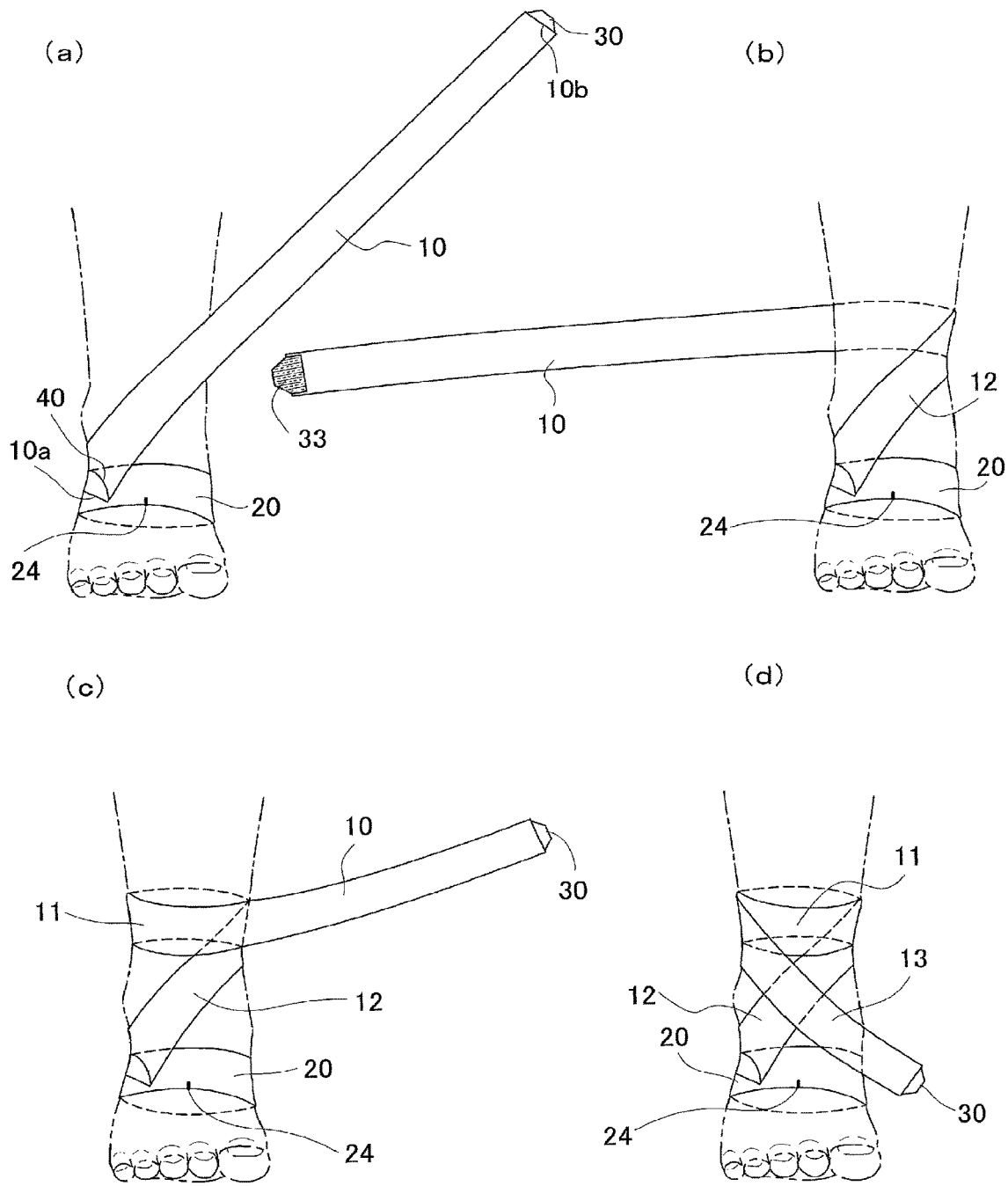
FIG. 7(a) is an explanatory diagram showing a state where the tiptoe of the right foot has been inserted into the anchor part of the ankle joint bandage shown in FIGS. 1 and 4.
FIG. 7(b) is an explanatory diagram showing a state where the main body part is half-turned from the internal malleolus of the right foot to the ankle.
FIG. 7(c) is an explanatory diagram showing a state where the main body part is further half-turned to the ankle from the state shown in FIG. 7(b)
FIG. 7(d) is an explanatory diagram showing a state where the main body part is disposed at the instep over an area from the external malleolus of the right foot to the first toe side.

Next, a method of wearing the ankle joint bandage 100 shown in FIGS. 1, 3, and 4 will be described by using FIGS. 6 and 7.

Figure 8:
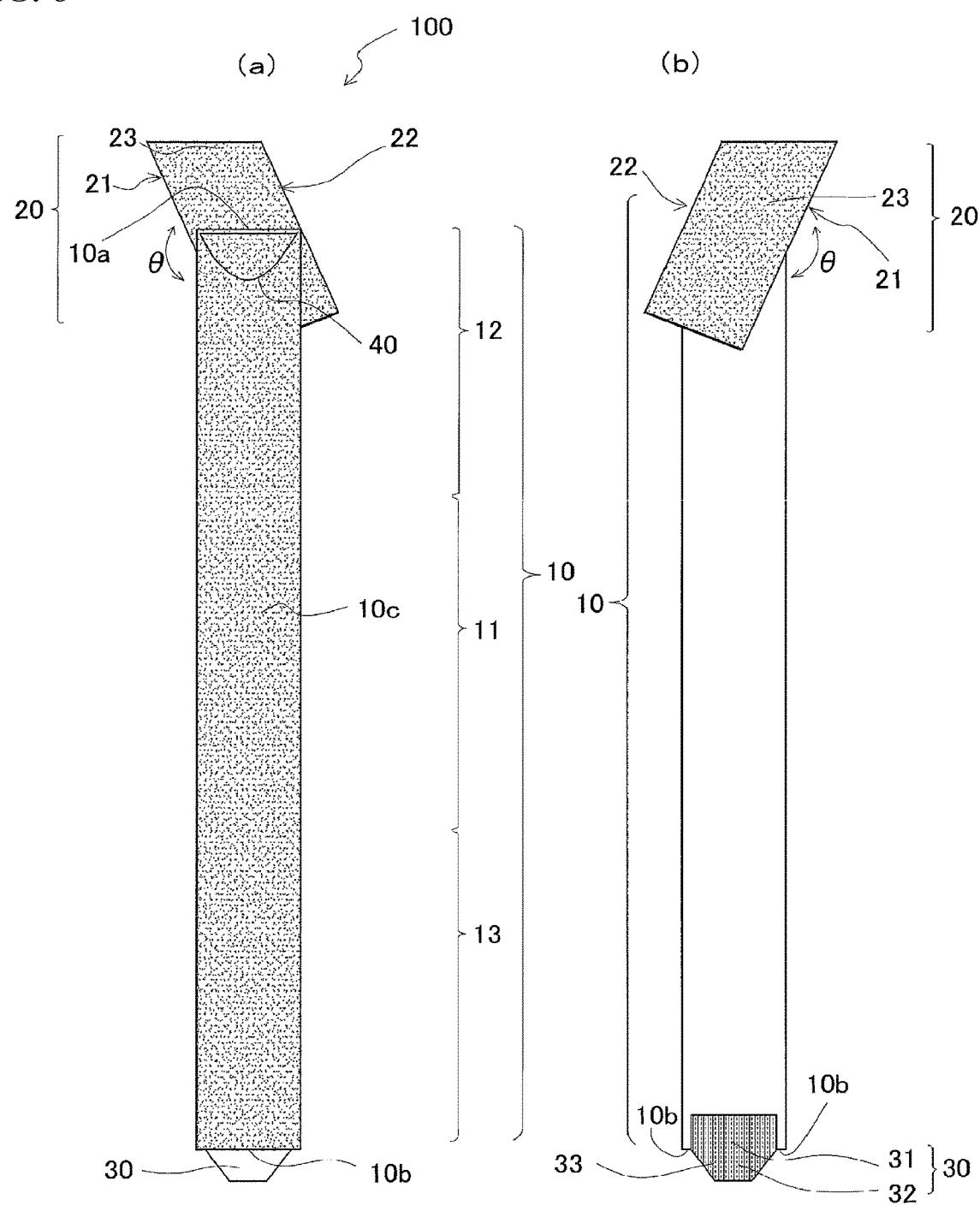
FIG. 8(a) is a front view showing a schematic configuration of an ankle joint bandage for left foot varus sprain prevention according to the first embodiment.
FIG. 8(b) is a back view of the ankle joint bandage shown in FIG. 8(a).
Figure 9:
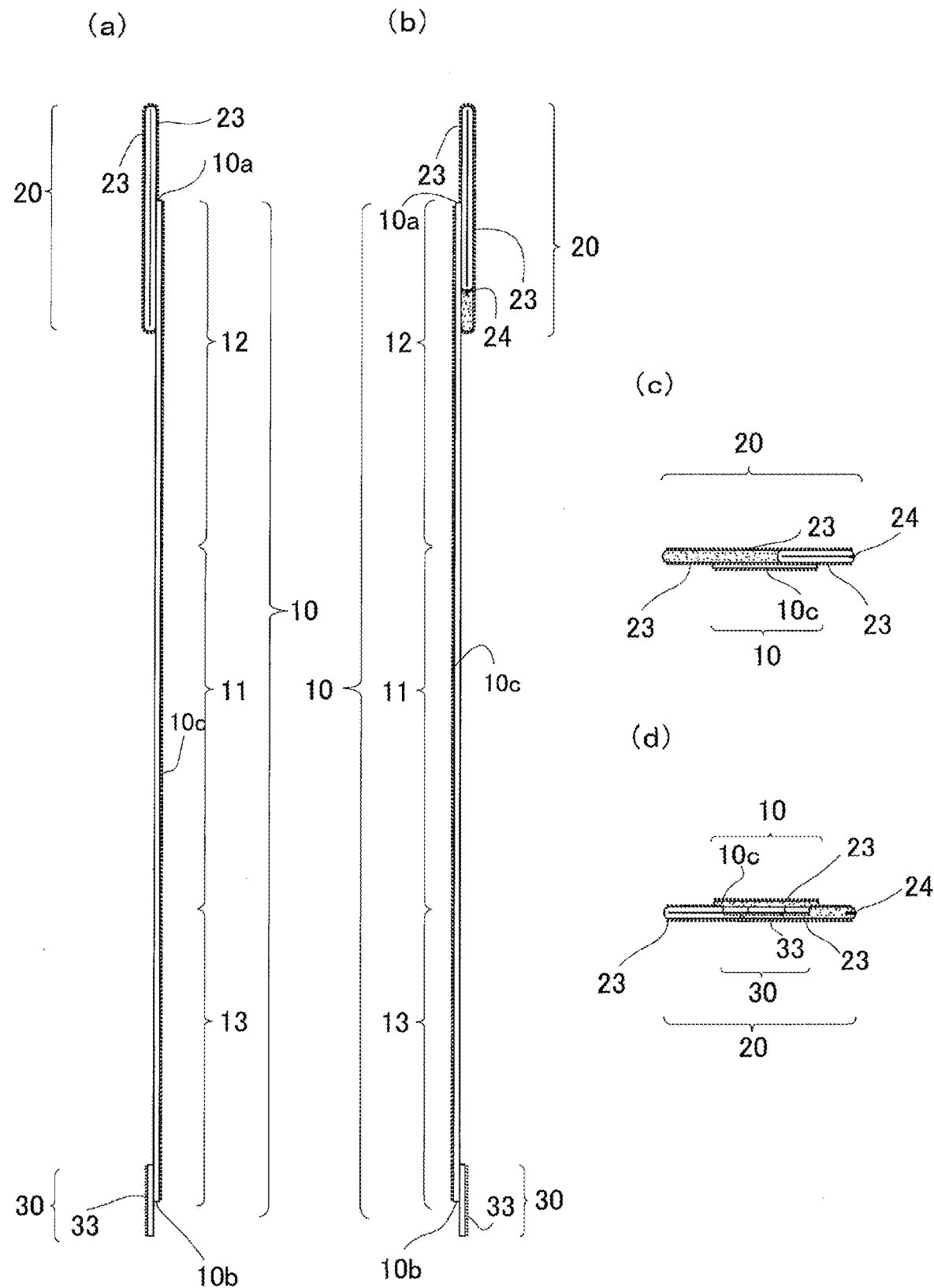
FIG. 9(a) is a left side view of the ankle joint bandage shown in FIG. 8(a)
FIG. 9(b) is a right side view of the ankle joint bandage shown in FIG. 8(a)
FIG. 9(c) is a plan view of the ankle joint bandage shown in FIG. 8(a)
FIG. 9(d) is a bottom view of the ankle joint bandage shown in FIG. 8(a).
Figure 10:
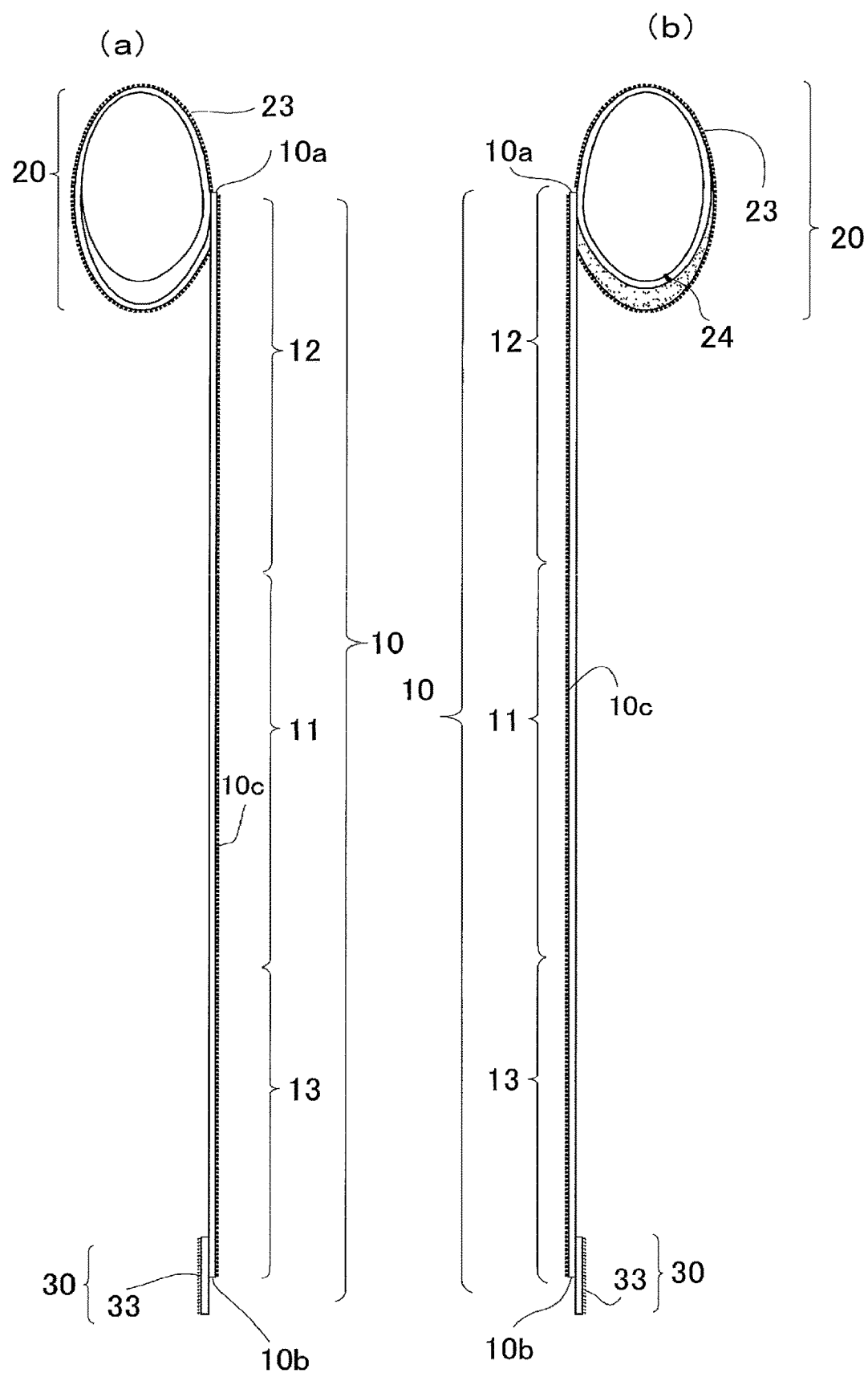
FIG. 10(a) is a left side view in which a main body part of the ankle joint bandage shown in FIG. 8(a) is shown in a ring shape.
FIG. 10(b) is a right side view in which the main body part of the ankle joint bandage shown in FIG. 8(a) is shown in a ring shape.

In addition, in the following description, a case of wearing the ankle joint bandage 100 on the right foot of a wearer will be described. However, in a case of wearing the ankle joint bandage 100 on the left foot of the wearer, the ankle joint bandage 100 shown in FIGS. 8, 9, and 10 is used, and wearing is performed with the "right foot" and the "left hand" in the following description respectively replaced by the "left foot" and the "right hand".

A wearer inserts the tiptoe of the right foot into the anchor part 20 of the ankle joint bandage 100, pushes the anchor part 20 to a part corresponding to the metatarsal bone, and fits the center mark 24 of the anchor part 20 to the center of the instep, as shown in FIG. 7(a).

Then, the wearer pulls the main body part 10 while gripping the other end 10b of the main body part 10 with the left hand and disposes the main body part 10 (the first supporting part 12) in an extended state at the instep over an area from the fifth toe side to the internal malleolus of the right foot. In addition, the extended state refers to a state of having an elongation margin allowing the wearer to finely adjust a winding position after the wearing of the ankle joint bandage 100.

Next, the wearer makes the main body part 10 (the winding part 11) in an extended state circle around the ankle by one round and a half in a direction of the external malleolus through the part corresponding to the Achilles' tendon from the internal malleolus of the right foot by using both hands, as shown in FIGS. 7(b) and 7(c).

Then, the wearer disposes the main body part 10 (the second supporting part 13) in an extended state on the instep over an area from the external malleolus to the first toe side of the right foot while gripping the other end 10b of the main body part 10 with the left hand, as shown in FIG. 7(d).

Finally, the wearer makes the hook face 33 of the engaging part 30 which is located at the other end 10b of the main body part 10 be engaged with the loop face 23 of the anchor part 20 which is located at the arch of the foot, as shown in FIG. 6, whereby the wearing is completed.

In this manner, in the ankle joint bandage 100, the engaging part 30 is engaged with the anchor part 20 which is located at the arch of the foot of the wearer, whereby it is possible to push up the arch of the foot of the wearer, and it is possible to improve a feeling of wearing of the wearer and an effect feeling.

Figure 3:
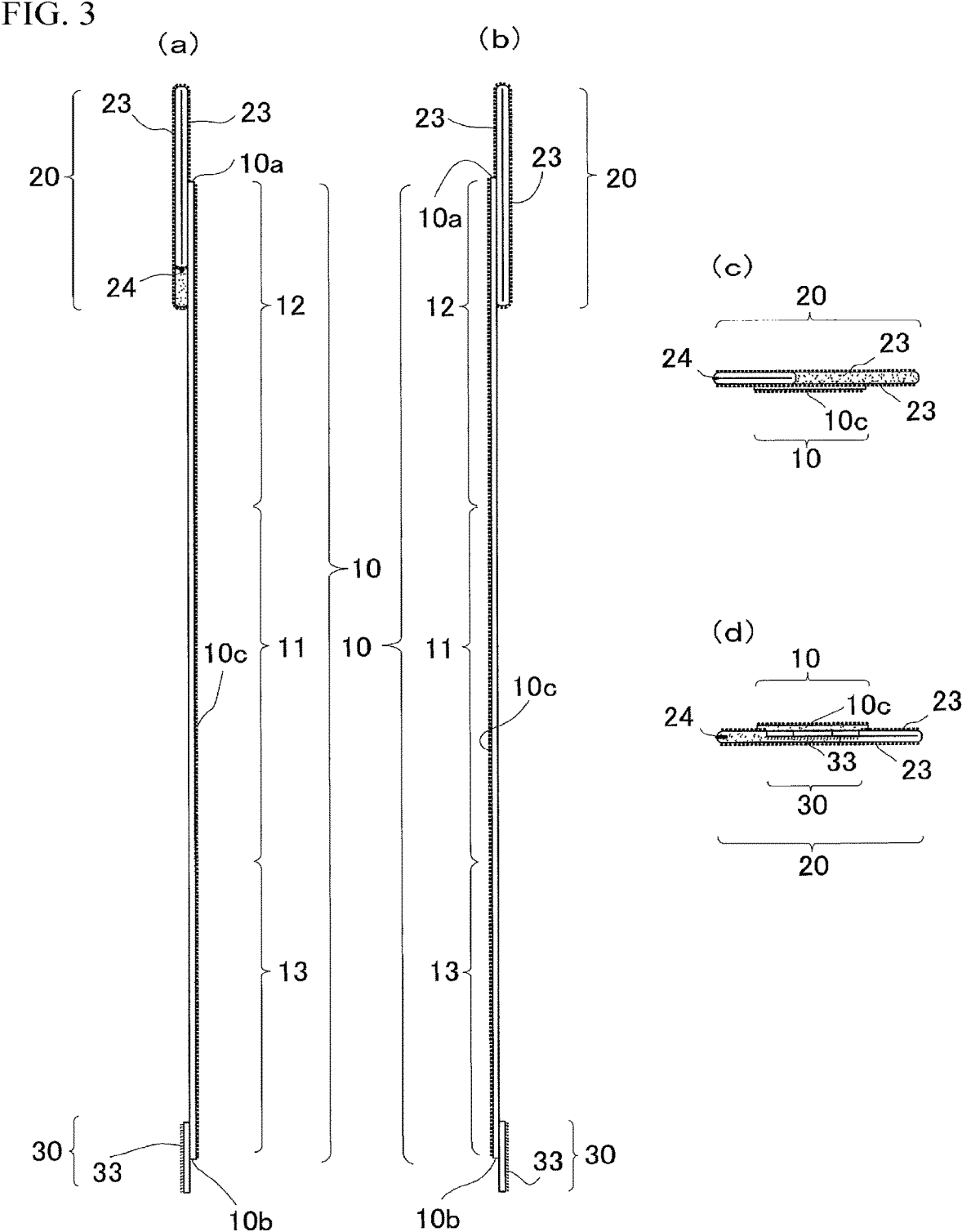
FIG. 3(a) is a left side view of the ankle joint bandage shown in FIG. 1(a)
FIG. 3(b) is a right side view of the ankle joint bandage shown in FIG. 1(a)
FIG. 3(c) is a plan view of the ankle joint bandage shown in FIG. 1(a)
FIG. 3(d) is a bottom view of the ankle joint bandage shown in FIG. 1(a).
Figure 4:
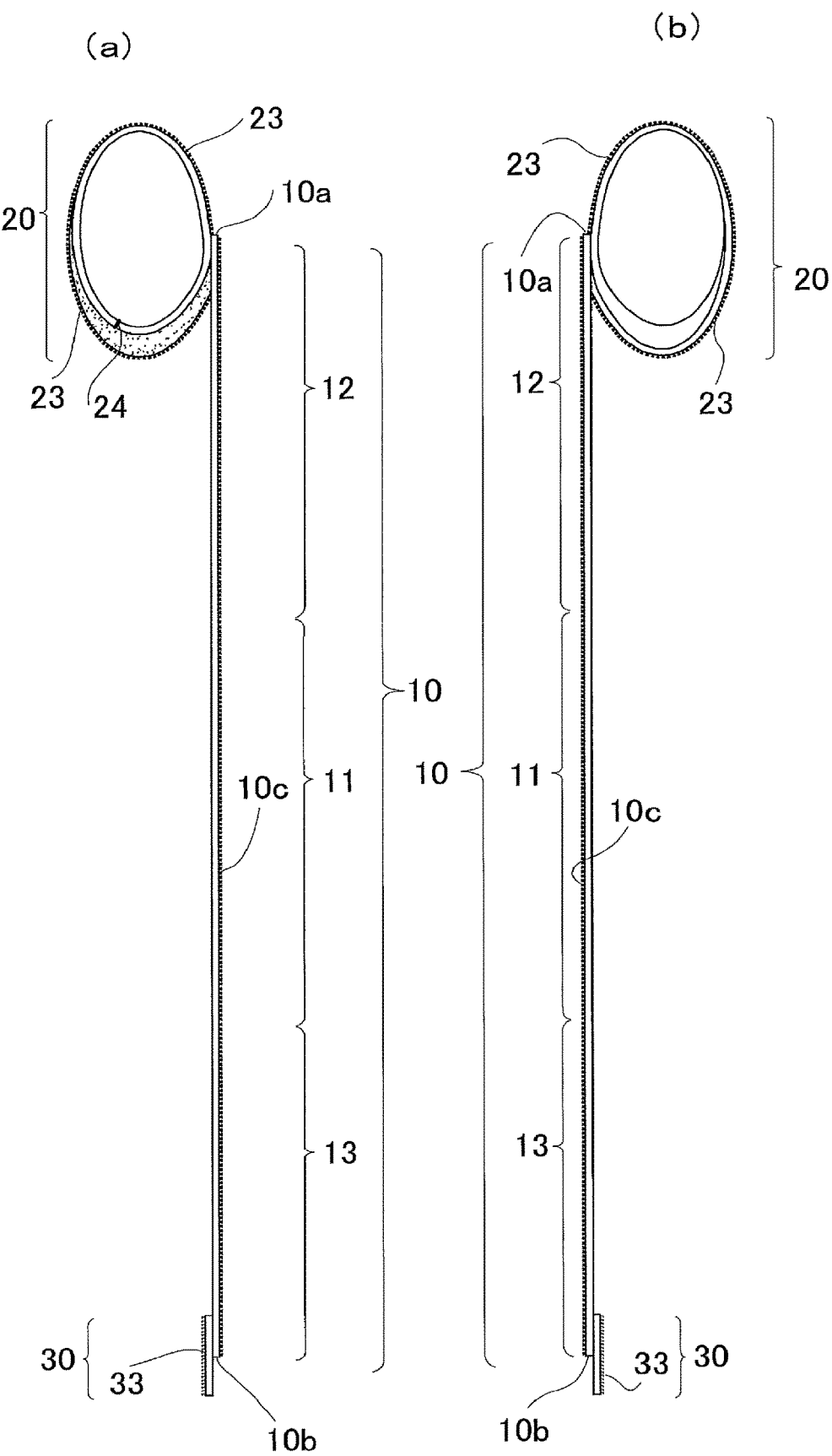
FIG. 4(a) is a left side view in which the main body part of the ankle joint bandage shown in FIG. 1(a) is shown in a ring shape.
FIG. 4(b) is a right side view in which the main body part of the ankle joint bandage shown in FIG. 1(a) is shown in a ring shape.

Further, in the ankle joint bandage 100 shown in FIGS. 1, 3, and 4, in the wearing method of the ankle joint bandage 100 described above, the main body part 10 (the first supporting part 12) is disposed over an area from the fifth toe side to the internal malleolus of the right foot, and thereafter, the main body part 10 (the winding part 11) is wound around the ankle in a counterclockwise direction. For this reason, in case where the ankle joint bandage 100 shown in FIGS. 1, 3, and 4 is worn on the right foot, the direction of winding start of the main body part 10 (the first supporting part 12) from the anchor part 20 becomes a direction from the outside of the right foot to the inside through the instep, and a force is applied in a valgus direction of the foot region in advance, and whereby it is possible to prevent a varus sprain developed when the ankle joint is twisted to the inside.

Further, as necessary, in a case where the ankle joint bandage 100 shown in FIGS. 1, 3, and 4 is worn on the left foot, the direction of winding start of the main body part 10 (the first supporting part 12) from the anchor part 20 becomes a direction from the inside of the left foot to the outside through the instep, and a force is applied in a varus direction of the foot region in advance, and whereby it is possible to prevent a valgus sprain developed when the ankle joint is twisted to the outside.

In contrast, with respect to the ankle joint bandage 100 shown in FIGS. 8, 9, and 10, in a case where the ankle joint bandage 100 is worn on the left foot, the main body part 10 (the first supporting part 12) is disposed over an area from the fifth toe side to the internal malleolus of the left foot, and thereafter, the main body part 10 (the winding part 11) is wound around the ankle in a clockwise direction. In this way, in a case where the ankle joint bandage 100 shown in FIGS. 8, 9, and 10 is worn on the left foot, the direction of winding start of the main body part 10 (the first supporting part 12) from the anchor part 20 becomes a direction from the outside of the left foot to the inside through the instep, and a force is applied in a valgus direction of the foot region in advance, and whereby it is possible to prevent a varus sprain developed when the ankle joint is twisted to the inside.

Further, as necessary, in a case where the ankle joint bandage 100 shown in FIGS. 8, 9, and 10 is worn on the right foot, the direction of winding start of the main body part 10 (the first supporting part 12) from the anchor part 20 becomes a direction from the inside of the right foot to the outside through the instep, and a force is applied in a varus direction of the foot region in advance, and thus it is also possible to prevent a valgus sprain.

Further, the ankle joint bandage 100 shown in FIGS. 8, 9, and 10 has a structure in which one end 10a of the main body part 10 of the ankle joint bandage 100 shown in FIGS. 1, 3, and 4 is joined at a line-symmetric position on the basis of the center mark 24 in the anchor part 20.

Next, the optimal range of the maximum elongation in the warp direction in the main body part 10 of the ankle joint bandage 100 according to this embodiment will be described based on the test results of a trial use test.

In addition, in the trial use test, as shown in FIG. 1, the ankle joint bandages 100 (hereinafter, respectively referred to as Example 1, Example 2, and Example 3) each provided with the main body part 10 (length: 50 cm, width: 5 cm) woven with the quality of the materials of the warp 1 and the weft 2 and the number of times of picking (the number) of the weft 2 shown in Table 1 below and having the maximum elongation of 45%, 60%, or 75%, the anchor part 20, and the engaging part 30 were fabricated and used.

Further, ankle joint bandages (hereinafter, respectively referred to as Comparative Example 1 and Comparative Example 2) were fabricated in the same manner as in the above examples by using the main body part 10 (length: 50 cm, width: 5 cm) having the maximum elongation of 35% or 90% and used in the trial use test.

TABLE 1

| | Quality of material | | | | | Number of times of picking | |
|---|---|---|---|---|---|---|---|
| | Warp | | | Weft | | | |
| | Warp ground yarn | Pile yarn | Elastic yarn | Weft ground yarn | Fusion yarn | (Number) of weft [times/inch] | Maximum elongation [%] |
| Example 1 | WN100/2 | 210D-10F | 560D | EW150D | Elder100D | 42.3 | 45 |
| Example 2 | WN100/2 | 210D-10F | 560D | EW150D | Elder100D | 36.9 | 60 |
| Example 3 | WN100/2 | 210D-10F | 560D | EW150D | Elder100D | 33.8 | 75 |
| Comparative Example 1 | WN100/2 | 210D-10F | 560D | EW150D | Elder100D | 42.3 | 35 |
| Comparative Example 2 | WN100/2 | 210D-10F | 560D | EW150D | Elder100D | 30.8 | 90 |

In the trial use test, the ankle joint bandage was worn on the right foot of the wearer, as shown in FIG. 6, and the sensory evaluation (a total of five persons) of an effect feeling of the wearer in the evaluation items of FIG. 13 was carried out. In an evaluation method, first, the sensory evaluation for each evaluation item in each wearer was scored in three stages (3: very good, 2: good, and 1: poor), and the average score of all the wearers (5 persons) in each evaluation item was calculated. Thereafter, with respect to Examples 1 to 3 and Comparative Examples 1 and 2, the total points and the average score of each evaluation item were calculated, and comprehensively, the average score of two or more points was determined to be a passing mark.

Further, with respect to the evaluation item "fixing force" of FIG. 13, if it is a force restraining a range of motion of plantar flexion or dorsal flexion of the ankle joint, restraint of the range of motion of the plantar flexion or the dorsal flexion of the ankle joint using a force more than necessary in a movement such as walking, running, or going up and down stairs is supposed. Further, if it is a force restraining ranges of motion of a varus and a valgus of the foot region, a case of using a force more than necessary at the time of a side step during sport, a stop movement at the time of a dash, or a daily movement such as holding-out in an unstable location such as a step, or restraint of a movement exceeding a limit of a range of motion is supposed.

Further, with respect to the evaluation item "pain" of FIG. 13, if it is a pain due to a compression force of the fabric, in a case where the maximum elongation of the fabric is small, the fabric cannot follow the movement of a muscle or a joint or the expansion and contraction of the skin, and the compression force is more strongly felt, and thus it is considered that a pain is easily felt, and in a case where the maximum elongation of the fabric is large, it is considered that the fixing force to restrain the range of motion becomes weaker.

Further, if it is a rubbing pain due to the hardness of the fabric, in a case where the maximum elongation of the fabric is small, the fabric cannot follow the movement of a muscle or the skin, and therefore, rubbing occurs between the fabric and the skin, and thus it is considered that a pain is easily felt, and in a case where the maximum elongation of the fabric is large, the fabric extends so as to follow a muscle or the skin, and therefore, it is considered that trouble to the skin is less.

Further, with respect to the evaluation item "ease of peeling-off of touch fastener" of FIG. 13, a touch fastener being easily peeled off means that even a powerless wearer does not have difficulty in using a touch fastener and the fabric itself having the loop face of a touch fastener is hard, whereby it is difficult to lose a shape.

Further, a touch fastener being not easily peeled off means that at the time of the wearer's movement, there is no case where the hook face of a touch fastener is separated from the loop face due to the movement of a joint or the expansion of a muscle in a site on which the bandage is worn, whereas the pile yarns are pulled out from the fabric having the loop face of a touch fastener due to a strong engaging force between the hook face and the loop face of a touch fastener, and thus, in a case where a touch fastener is peeled off, the pile yarns project from the fabric, thereby causing fluffing of the fabric.

Further, with respect to the evaluation item "close contact property of fabric" of FIG. 13, in a case where the maximum elongation of the fabric is small, the fabric cannot follow the movement of a muscle or the skin, and therefore, a cloth does not come into close contact with the skin and skin resistance is reduced, and thus it is considered that the effect of the bandage is weakened, and in a case where the maximum elongation of the fabric is large, a cloth is easily fixed in close contact with the skin and fits to the movement of the skin or a muscle, and thus it is considered that the effect of the bandage is easily obtained.

Further, with respect to the evaluation item "ease of winding" of FIG. 13, in a case where the maximum elongation of the fabric is small, it is difficult for the fabric to conform to the curved surface of the skin, and thus it is difficult to wind the main body part 10. Further, in a case where the maximum elongation of the fabric is large, the fabric is easily fixed in close contact with the skin and easily fits to the movement of the skin or a muscle. However, for effective wearing, it is necessary to wind the main body part 10 while fully extending it. However, if the main body part 10 is fully extended, the distance between the hand holding the other end 10b of the main body part 10 and the anchor part 20 becomes longer, and therefore, the wearing and winding on the ankle joint becomes difficult. Further, it becomes difficult to fix the other end 10b of the main body part 10 to a predetermined position of the anchor part 20, and therefore, a movement to wind the main body part 10 while performing seeking so as to be able to fix the other end 10b of the main body part 10 to a predetermined position is performed.

Further, with respect to the evaluation item "ease of adjustment of fixing force" of FIG. 13, in a case where the maximum elongation of the fabric is small, it is suitable for strong fixing. However, an adjustable range of the fixing force is narrow, and therefore, adjustment of the fixing force becomes difficult for a powerless wearer.

Further, with respect to the evaluation item "difficulty of fabric folding" of FIG. 13, in a case where the maximum elongation of the fabric is small, a texture is close, and therefore, there is also stiffness of the fabric, and thus it is difficult for the fabric to be folded. Further, in a case where the maximum elongation of the fabric is large, a texture is rough, and therefore, the fabric has an easily foldable weave, and thus it is considered that due to the fabric being folded, the structure of the main body part 10 is weakened.

In the evaluation items as described above, in Example 2, good evaluation results were obtained in almost all the evaluation items, as shown in FIG. 13.

Further, in Example 3, although the fixing force was weak, good evaluation results were obtained in other evaluation items.

Further, in Example 1, although there was a pain and the close contact property of the fabric was poor, good evaluation results were obtained in other evaluation items. In contrast, in Comparative Example 1 and Comparative Example 2, poor evaluation results were obtained in most of the evaluation items.

From the above, as the overall evaluation results, it is found that Example 1 (maximum elongation: 45%), Example 2 (maximum elongation: 60%), and Example 3 (maximum elongation: 75%), in which the average score is two or more points, are optimal as the main body part 10.

That is, with respect to the maximum elongation in the warp direction in the main body part 10 of the ankle joint bandage 100 according to this embodiment, a range of 40% to 80% is preferable, a range of 45% to 75% is more preferable, and the most preferred is 60%.

Next, the anchor part 20 of the ankle joint bandage 100 according to this embodiment will be described based on the test results of a durability test (peeling strength) of a touch fastener.

In addition, in the durability test (peeling strength) of a touch fastener, on the basis of Example 2 (the anchor part 20 in which the maximum elongation in the warp direction is 60%) in which the most favorable results were obtained from the evaluation results of the above-described sensory evaluation, comparison with other stretchable fabrics was performed. Further, as comparative examples, commercially available stretchable fabrics (hereinafter, respectively referred to as Comparative Example 3, Comparative Example 4, and Comparative Example 5) made with the quality of the materials of the warp 1 and the weft 2 and the number of times of picking (the number) of the weft 2 shown in Table 2 below were used. In addition, Comparative Example 3 does not have a loop face as a touch fastener, and therefore, Comparative Example 3 is not provided with a pile yarn in a warp and a fusion yarn in a weft.

TABLE 2

|  | Quality of material | | | | | Number of times of picking | | | |
|---|---|---|---|---|---|---|---|---|---|
|  | Warp | | | Weft | | (Number) | | | |
|  | Warp ground yarn | Pile yarn | Elastic yarn | Weft ground yarn | Fusion yarn | of weft [times/inch] | Thickness [mm] | Hardness | Maximum elongation [%] |
| Example 2 | WN100/2 | 210D-10F | 560D | EW150D | Elder 100D | 36.9 | 2.1 | Slightly soft | 60 |
| Comparative Example 3 | WN100/2 | — | 1120D | Nylon monofilament No. 1 | — | 37.0 | 1.7 | Soft | 130 |
| Comparative Example 4 | WN100/2 | 210D-7F | 1120D | EW300D | Elder 100D | 43.6 | 2.2 | Normal | 90 |
| Comparative Example 5 | WN100/2 | 210D-15F | 1120D | EW300D | Elder 100D | 25.8 | 3.3 | Hard | 100 |

Further, the major difference between Example 2 and Comparative Examples 3 to 5 is a difference in the filament count of the pile yarn, in which Example 2 has 10 pieces of filaments, whereas Comparative Example 4 has 7 pieces of filaments, Comparative Example 5 has 15 pieces of filaments, and Comparative Example 3 does not use a pile yarn (does not have a loop face of a touch fastener).

The durability test (peeling strength) of a touch fastener is based on Japanese Industrial Standards JIS L3416, "touch fastener", 7.4.2 "peeling strength", and the experimental results obtained by carrying out a repeat of adhesion and peeling 1000 times are shown in Table 3 below.

TABLE 3

|  | Effective width of fastener [cm] | Peeling strength [N/cm] | | Retention rate [%] (peeling strength after durability test/initial peeling strength × 100) | Change in appearance after durability test |
|---|---|---|---|---|---|
| Example 2 | 4.7 | Initial | 0.358 | 181 | Loop elongation which is less (than |
|  |  | After | 0.649 |  |  |

TABLE 3-continued

|  | Effective width of fastener [cm] | Peeling strength [N/cm] | | Retention rate [%] (peeling strength after durability test/initial peeling strength × 100) | Change in appearance after durability test |
|---|---|---|---|---|---|
|  |  | durability test |  |  | Comparative Example 5) is recognized. |
| Comparative Example 3 | 4.8 | Initial After durability test | 0.996 0.825 | 83 | Violent fluffing is recognized. |
| Comparative Example 4 | 4.7 | Initial After durability test | 0.281 0.254 | 90 | Noticeable change is not recognized. |
| Comparative Example 5 | 2.8 | Initial After durability test | 0.326 0.537 | 165 | Slight loop elongation is recognized. |

In Example 2, as shown in Table 3, the retention rate (the percentage of peeling strength after durability test with respect to initial peeling strength) is the highest, compared to Comparative Examples 3 to 5, and thus it is found that Example 2 is optimal as the anchor part 20 which is used in the ankle joint bandage 100 which is wound around the ankle joint and then engaged by the hooks of a touch fastener.

In particular, in Example 2, the peeling strength after durability test becomes larger with respect to the initial peeling strength (the retention rate exceeds 100%), and therefore, Example 2 is advantageous in terms of a long-term continuing use as the ankle joint bandage 100.

Further, the filament count of the pile yarn being high means that the hooks of a touch fastener are easily engaged with the loops and the retention rate is increased, while the maximum elongation is lowered.

In Comparative Example 5, the filament count of the pile yarn is higher than the filament count of the pile yarn of Example 2. However, resin processing is applied in order to prevent fluffing of external appearance, and therefore, it becomes difficult for the hooks of a touch fastener to be engaged with the loops, and the initial peeling strength and the retention rate become lower than the initial peeling strength and the retention rate of Example 2.

As described above, the ankle joint bandage 100 fixes the talocrural joint of a wearer by configuring a figure-eight with the main body part 10, establishes joint compatibility, stabilizes the ankle joint, and suppresses (heel locking) the deflection of the ankle of a wearer during walking, thereby preventing a varus sprain or eliminating instability or the like at the time of standing on one leg, and thus it is possible to support stable walking of the wearer.

Further, the figure-eight by the main body part 10 assists the dorsal flexion braking of the ankle joint, thereby being able to lead the center of gravity of a wearer in the direction of the tiptoe and assist the walking of the wearer. Further, the figure-eight by the main body part 10 can stabilize the ankle joint of a wearer and perform assistance for absorbing an impact from the ground (a floor) in the initial stage of a stance phase (a period in which the foot during walking is in contact with the ground).

In particular, the ankle joint bandage 100 exhibits the operation and effects which can contribute to impact absorption in the initial stage of a stance phase and a propulsive force over a stage from the intermediate stage to the late stage of the stance phase and allow the stability of the ankle joint to be obtained by the left and right (varus and valgus) braking.

Further, the ankle joint bandage 100 exhibits the operation and effects which assist the ankle joint of a wearer, thereby being able to relieve a pain of the Achilles' tendon, fatigue and a pain of the triceps surae muscle, and a pain of the outside (the ligament) of the ankle joint.

Further, in the ankle joint bandage 100 shown in FIG. 2, for example, green yarns are used for the warp ground yarns 1*a* of the warps 1 of the main body part 10 and the anchor part 20, black yarns are used for the pile yarns 1*b* of the warps 1 of the main body part 10 and the anchor part 20, black yarns are used for the elastic yarns 1*c* of the warps 1 of the main body part 10 and the anchor part 20, black yarns are used for the wefts 2 of the main body part 10 and the anchor part 20, and as shown in FIG. 12, with respect to the shared weft 2, the warp ground yarn 1*a* is made to float and the pile yarn 1*b* is made to sink, whereby a green pattern 14 is formed on a black front ground face and the portions of the back ground faces of the main body part 10 and the anchor part 20, which correspond to the patterns 14 of the front ground faces of the main body part 10 and the anchor part 20, appear as black on green back ground faces of the main body part 10 and the anchor part 20.

Further, in the ankle joint bandage 100, there is no limitation to these colors, and for example, it is conceivable that a yarn having any one color of seven colors (red, orange, yellow, green, blue, indigo, and violet) which are the rainbow colors is used for the pile yarn 1*b* of the warp 1 of each of the main body part 10 and the anchor part 20 and the front ground face except for the pattern 14 of each of the main body part 10 and the anchor part 20 is made to have any one color of the rainbow colors. In this way, the ankle joint bandages 100 can encourage a consumer's willingness to buy with product groups with color variation of seven colors.

Further, in the ankle joint bandage 100, for example, the front ground face except for the pattern 14 of each of the main body part 10 and the anchor part 20 is made to have a fluorescent color by using a fluorescent colored yarn for the pile yarn 1*b* of the warp 1 of each of the main body part 10 and the anchor part 20, whereby a consumer's willingness to buy is encouraged, and the ankle joint bandage 100 is worn during going out at night, whereby it is visible by being illuminated by the headlights of an automobile or the like, and thus it can be expected to contribute to the safety and disaster prevention as well.

Figure 14:
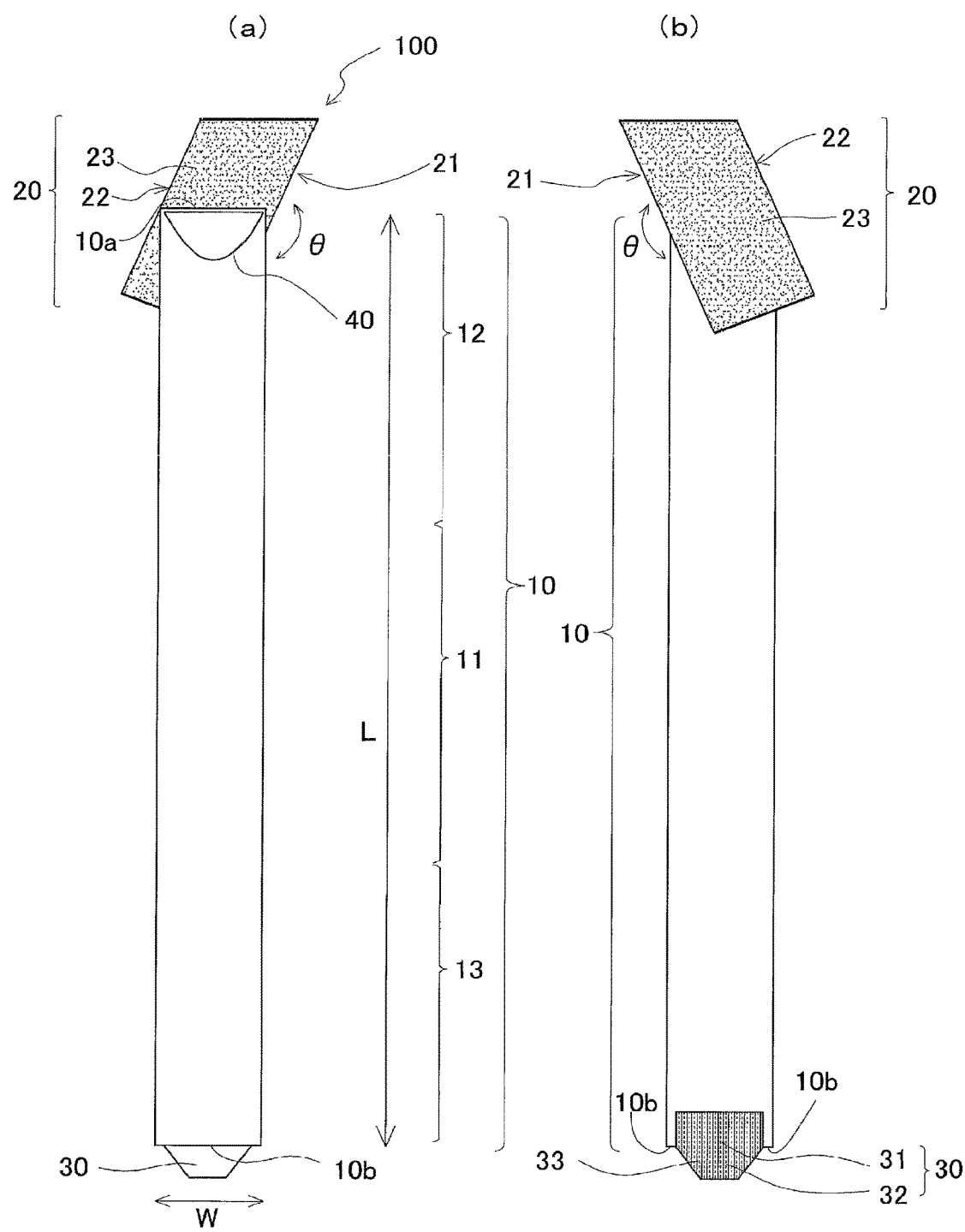
FIG. 14(a) is a front view showing a schematic configuration of another ankle joint bandage for right foot varus sprain prevention according to the first embodiment.
FIG. 14(b) is a back view of the ankle joint bandage shown in FIG. 14(a).

Further, a case where the main body part 10 according to this embodiment has the loop face 10c of a touch fastener has been described. However, as shown in FIG. 14, a stretchable fabric which does not have the loop face 10c of a touch fastener is also acceptable.

In this case, the main body part 10 does not need the pile yarn 1b forming the loop face 10c and does not need the fusion yarn 2b holding the loops by the pile yarn 1b.

In particular, the main body part 10 according to this embodiment uses, instead of the pile yarn 1b configuring the warp 1, a warp ground yarn 1a (hereinafter referred to as a second warp ground yarn 1d) in which float-sink with respect to the weft 2 is reversed with respect to that in the above-described warp ground yarn 1a (hereinafter referred to as a first warp ground yarn 1a).

Figure 15:
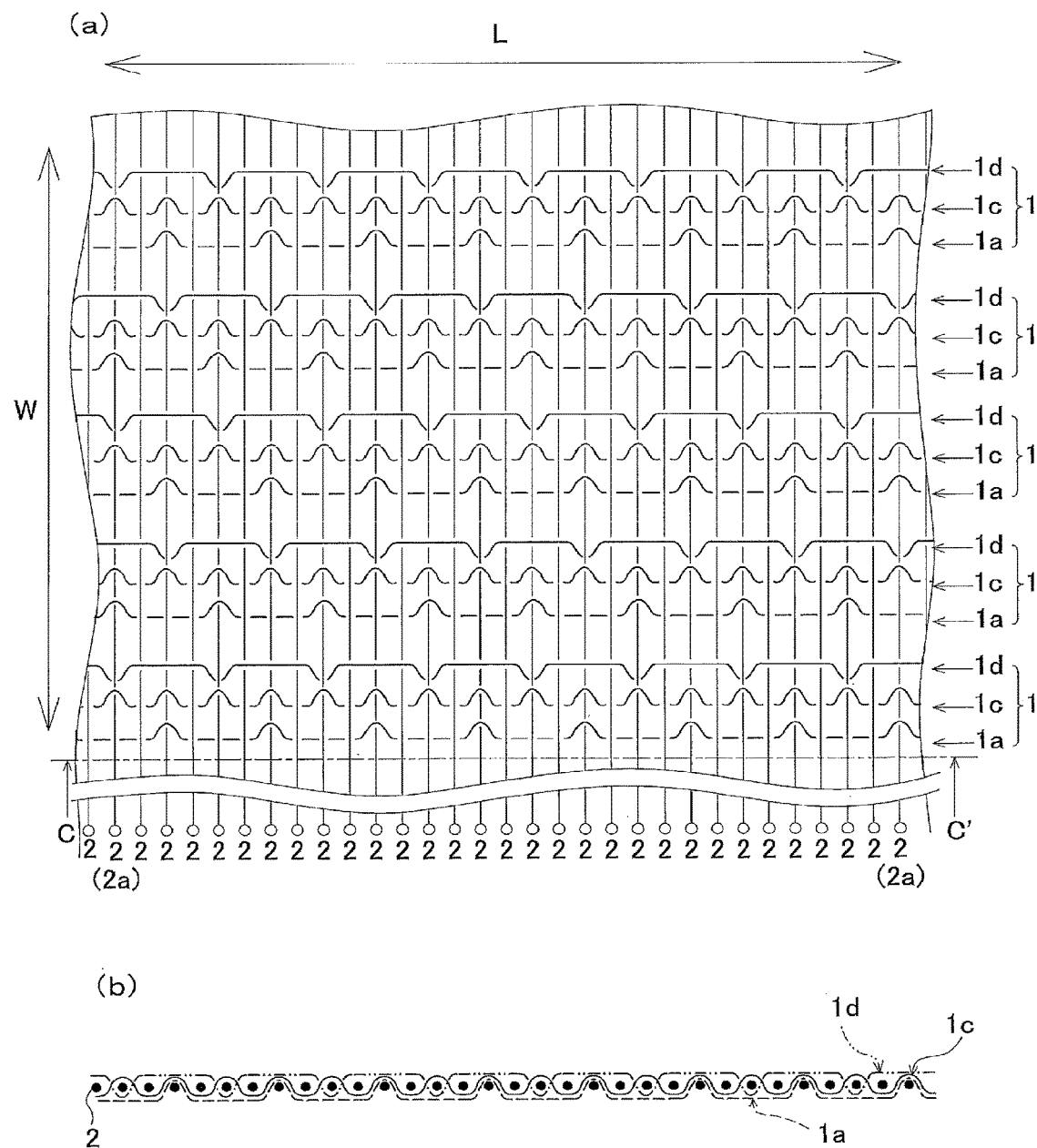
FIG. 15(a) is an explanatory diagram for describing an example of a fabric weave of a front ground face of the main body part shown in FIGS. 14(a) and 14(b)
FIG. 15(b) is a cross-sectional view taken along line C-C' and viewed in the direction of an arrow, of the fabric weave shown in FIG. 15(a).

That is, the warp 1 is provided with the first warp ground yarn 1a which configures one face (for example, the back ground face) of the fabric along with the weft 2, the elastic yarn 1c which provides stretchability in the warp direction, and the second warp ground yarn 1d which configures the other face (for example, the front ground face) of the fabric along with the weft 2, as shown in FIG. 15.

Further, the weft 2 is provided with the weft ground yarn 2a which configures the back ground face of the fabric along with the first warp ground yarn 1a.

Further, in FIGS. 15(b) and 16(b), on the basis of the wefts 2 which are provided in parallel, the upper side is the front ground face and the lower side is the back ground face.

Further, in the main body part 10, the pattern 14 composed of characters, figures, symbols, or a combination thereof can be partially formed in the front ground face in a jacquard weave which is freely opened, by making the first warp ground yarn 1a (for example, a green yarn) of the warp 1 float to the front ground face side (and making the second warp ground yarn 1d (for example, a black yarn) sink to the back ground face side) with respect to a plurality of wefts 2 adjacent to each other in the warp direction (the longitudinal direction L) by using a jacquard needle loom.

Next, an example of a fabric weave according to this embodiment will be described by using FIG. 15. That is, the first warp ground yarn 1a configures a fabric weave by repeating 1-3 float-sink with respect to the weft 2 (the weft ground yarn 2a), in which the first warp ground yarn 1a floats so as to pass on the upper side with respect to a single piece of weft 2 (weft ground yarn 2a) and sinks so as to pass on the lower side with respect to three pieces of wefts 2 (weft ground yarns 2a) adjacent to each other, as shown in FIG. 15(b).

Further, the elastic yarn 1c configures a fabric weave by repeating 1-1 float-sink with respect to the weft 2 (the weft ground yarn 2a), in which the elastic yarn 1c floats so as to pass on the upper side with respect to a single piece of weft 2 (weft ground yarn 2a) and sinks so as to pass on the lower side with respect to a single piece of weft 2 (weft ground yarn 2a), as shown in FIG. 15(b).

Further, the second warp ground yarn 1d configures a fabric weave by repeating 3-1 float-sink with respect to the weft 2 (the weft ground yarn 2a), in which the second warp ground yarn 1d floats so as to pass on the upper side with respect to three pieces of wefts 2 (weft ground yarns 2a) adjacent to each other and sinks so as to pass on the lower side with respect to a single piece of weft 2 (weft ground yarn 2a), as shown in FIG. 15(b).

In addition, the fabric weave composed of the first warp ground yarn 1a, the elastic yarn 1c, and the second warp ground yarn 1d shown in FIG. 15 is an example, and there is no limitation to this fabric weave.

Subsequently, an example of a fabric weave of a pattern part according to this embodiment will be described by using FIG. 16. That is, the first warp ground yarn 1a forming the pattern 14 configures a fabric weave by repeating 3-1 float-sink with respect to the weft 2 (the weft ground yarn 2a), in which the first warp ground yarn 1a floats so as to pass on the upper side with respect to three pieces of wefts 2 (weft ground yarns 2a) adjacent to each other and sinks so as to pass on the lower side with respect to a single piece of weft 2 (weft ground yarn 2a), as shown in FIG. 16(b).

Further, the elastic yarn 1c forming the pattern 14 configures a fabric weave by repeating 1-1 float-sink with respect to the weft 2 (the weft ground yarn 2a), in which the elastic yarn 1c floats so as to pass on the upper side with respect to a single piece of weft 2 (weft ground yarn 2a) and sinks so as to pass on the lower side with respect to a single piece of weft 2 (weft ground yarn 2a), as shown in FIG. 16(b).

Further, the second warp ground yarn 1d forming the pattern 14 configures a fabric weave by repeating 1-3 float-sink with respect to the weft 2 (the weft ground yarn 2a), in which the second warp ground yarn 1d floats so as to pass on the upper side with respect to a single piece of weft 2 (weft ground yarn 2a) and sinks so as to pass on the lower side with respect to three pieces of wefts 2 (weft ground yarns 2a) adjacent to each other, as shown in FIG. 16(b).

In addition, the fabric weave composed of the first warp ground yarn 1a, the elastic yarn 1c, and the second warp ground yarn 1d shown in FIG. 16 is an example, and as long as it is possible to form the pattern 14 in the front ground face, there is no limitation to this fabric weave.

Here, an embodiment in which the main body part 10 is a stretchable fabric which does not have the loop face 11 of a touch fastener and the maximum elongation of the main body part 10 is set to be 60% (1.60 times±0.1) will be described.

With respect to each of the first warp ground yarn 1a and the second warp ground yarn 1d of the main body part 10 according to this embodiment, a woolly nylon two-fold yarn having a thickness of 100 deniers is preferable, and in the main body part 10 according to this embodiment, it is preferable to use 152 pieces of woolly nylon two-fold yarns for each of the first warp ground yarn 1a and the second warp ground yarn 1d.

Further, with respect to the elastic yarn 1c of the main body part 10 according to this embodiment, a covering yarn obtained by covering a polyurethane yarn (for example, a polyurethane elastic fiber "Lycra (registered trademark) fiber" of Toray Opelontex Co., Ltd.) having a thickness of 560 deniers with two pieces of polyester woolly (EW) single yarns each having a thickness of 150 deniers is preferable, and in the main body part 10 according to this embodiment, it is preferable to use 41 pieces of covering yarns.

Further, with respect to the weft ground yarn 2a of the main body part 10 according to this embodiment, it is preferable to use a single piece of polyester woolly yarn (EW) having a thickness of 150 deniers.

Further, in the main body part 10 according to this embodiment, a single piece of weft ground yarn 2a is picked as the weft 2 by a power loom, and the number of times of picking (the number) of the weft 2 (the weft ground yarn 2a) is 33.6 times (33.6 pieces) per 2.54 cm (1 inch).

In this manner, in the main body part 10 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 60%.

Further, the main body part 10 according to this embodiment has a mixing ratio of nylon: 47%, polyester: 44%, and polyurethane: 9%. However, there is no limitation to this mixing ratio.

Further, a case where the ankle joint bandage 100 according to this embodiment is directly wound on the bare skin has been described. However, with respect to the ankle joint on which, for example, a foot joint supporter disclosed in Pamphlet of International Publication No. WO2011/090193 or a sock (foot covers, socks, stockings, or tights and panty-stockings) is worn, the ankle joint bandage 100 is wound on the foot joint supporter or the sock, thereby eliminating the slip of the ankle joint bandage 100 with respect to the bare skin, whereby it is possible to improve the operation and effects of the ankle joint bandage 100.

Further, in a case where the ankle joint bandage 100 is wound on the sock, it is also possible to provide the ankle joint bandage 100 and the sock as a set.

Further, in a case where the ankle joint bandage 100 is wound on the sock (a sock in which the maximum elongation is low is preferable), as an aspect of the ankle joint bandage 100, the anchor part 20 of the ankle joint bandage 100 is removed from the main body part 10 and one end 10a of the main body part 10 is sewn to the outer surface or the inner surface in the boundary between the instep part and the sole part of the sock, whereby it is possible to make the tiptoe part of the sock function as the anchor part 20.

REFERENCE SIGNS LIST

1: warp
1a: warp ground yarn (first warp ground yarn)
1b: pile yarn
1c: elastic yarn
1d: second warp ground yarn
2: weft
2a: weft ground yarn
2b: fusion yarn
10: main body part
10a: one end
10b: other end
10c: loop face
11: winding part
12: first supporting part
13: second supporting part
14: pattern
20: anchor part
21: large-diameter portion
22: small-diameter portion
23: loop face
24: center mark
30: engaging part
31: rectangular portion
32: isosceles trapezoid portion
33: hook face
40: joining portion
100: ankle joint bandage

The invention claimed is:

1. An ankle joint bandage, comprising:
a main body part comprising a woven fabric and having a band shape;
an anchor part joined to one end of the main body part, comprising a woven fabric in a ring shape, and having a loop face of a touch fastener; and
an engaging part joined to the other end of the main body part and having a hook face of a touch fastener,
wherein the main body part has a winding part configured to wind around an ankle of a wearer, a first supporting part configured to extend from an instep to the ankle of the wearer, and a second supporting part configured to extend from the ankle to the instep of the wearer and to cross the first supporting part at an upper portion of the instep of the wearer, the anchor part is configured to fasten around a part corresponding to a metatarsal bone of the wearer, the engaging part detachably sticks to the loop face of the anchor part, and the anchor part is joined to the main body part such that a circumferential direction of the ring shape of the anchor part forms an angle with respect to a longitudinal direction of the main body part at the angle in a range of 145° to 165° between the circumferential direction of the anchor part and the longitudinal direction of the main body part.

2. The ankle joint bandage according to claim 1, wherein the main body part has the first supporting part formed on one end side of the main body part, the second supporting part formed on the other end side of the main body part, and the winding part formed between the first supporting part and the second supporting part, and the first supporting part, the winding part, and the second supporting part have straight line shapes having the same width.

3. The ankle joint bandage according to claim 2, wherein the main body part has a maximum elongation in a range of 40% to 80% in a longitudinal direction of the main body part.

4. The ankle joint bandage according to claim 3, wherein the anchor part has a joining portion joined to the one end of the main body part and sewn in a convex shape toward the other end side of the main body part such that the convex shape is longer than a length in a width direction of the main body part.

5. The ankle joint bandage according to claim 4, wherein the anchor part has a substantially conical tube form.

6. The ankle joint bandage according to claim 3, wherein the anchor part has a substantially conical tube form.

7. The ankle joint bandage according to claim 2, wherein the anchor part has a joining portion joined to the one end of the main body part and sewn in a convex shape toward the other end side of the main body part such that the convex shape is longer than a length in a width direction of the main body part.

8. The ankle joint bandage according to claim 7, wherein the anchor part has a substantially conical tube form.

9. The ankle joint bandage according to claim 2, wherein the anchor part has a substantially conical tube form.

10. The ankle joint bandage according to claim 2, wherein the main body part has a front ground face having a pattern including at least one of a character, a figure and a symbol.

11. The ankle joint bandage according to claim 1, wherein the main body part has a maximum elongation in a range of 40% to 80% in a longitudinal direction of the main body part.

12. The ankle joint bandage according to claim 11, wherein the anchor part has a joining portion joined to the one end of the main body part and sewn in a convex shape toward the other end side of the main body part such that the convex shape is longer than a length in a width direction of the main body part.

13. The ankle joint bandage according to claim 12, wherein the anchor part has a substantially conical tube form.

14. The ankle joint bandage according to claim 11, wherein the anchor part has a substantially conical tube form.

15. The ankle joint bandage according to claim 11, wherein the main body part has a front ground face having a pattern including at least one of a character, a figure and a symbol.

16. The ankle joint bandage according to claim 1, wherein the anchor part has a joining portion joined to the one end of the main body part and sewn in a convex shape toward the other end side of the main body part such that the convex shape is longer than a length in a width direction of the main body part.

17. The ankle joint bandage according to claim 16, wherein the anchor part has a substantially conical tube form.

18. The ankle joint bandage according to claim 16, wherein the main body part has a front ground face having a pattern including at least one of a character, a figure and a symbol.

19. The ankle joint bandage according to claim 1, wherein the anchor part has a substantially conical tube form.

20. The ankle joint bandage according to claim 1, wherein the main body part has a front ground face having a pattern including at least one of a character, a figure and a symbol.

\* \* \* \* \*